(12) United States Patent
Cormier et al.

(10) Patent No.: US 9,579,139 B2
(45) Date of Patent: *Feb. 28, 2017

(54) DEVICES AND METHODS FOR BREAKING AND RETAINING SURGICAL REDUCTION TABS

(71) Applicant: DePuy Synthes Products, Inc., Raynham, MA (US)

(72) Inventors: Philip A. Cormier, Quincy, MA (US); Richard W. Fournier, New Bedford, MA (US); Ernest Quintanilha, Norton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/193,857

(22) Filed: Jun. 27, 2016

(65) Prior Publication Data

US 2016/0302838 A1    Oct. 20, 2016

Related U.S. Application Data

(63) Continuation of application No. 14/021,203, filed on Sep. 9, 2013, now Pat. No. 9,402,673.

(Continued)

(51) Int. Cl.
  *A61B 17/88* (2006.01)
  *A61B 17/70* (2006.01)
  *A61B 17/00* (2006.01)

(52) U.S. Cl.
  CPC ...... *A61B 17/8863* (2013.01); *A61B 17/7074* (2013.01); *A61B 2017/00429* (2013.01)

(58) Field of Classification Search
  CPC .......... A61B 17/708; A61B 17/7032–17/7047; A61B 17/7074–17/7091; A61B 17/8863

(Continued)

(56) References Cited

U.S. PATENT DOCUMENTS 3,343,443 A * 9/1967 Moore .................. F16B 19/083
                                                      29/432
5,362,166 A * 11/1994 Yamamoto .......... B43L 19/0056
                                                      15/433

(Continued)

OTHER PUBLICATIONS

Surgical Technique Guide and Ordering Information. DePuy Spine Inc. 2011. 24 pages.

(Continued)

*Primary Examiner* — Christian Sevilla
*Assistant Examiner* — Eric S Gibson
(74) *Attorney, Agent, or Firm* — Nutter McClennen & Fish LLP

(57) ABSTRACT

Various devices and methods for breaking and retaining surgical reduction tabs are provided. In general, the devices and methods can allow a single surgical instrument to break a plurality of surgical reduction tabs off one or more surgical implants and retain the broken tabs within the instrument. In an exemplary embodiment, a surgical instrument can include an opening at a distal end thereof that is configured to receive a surgical reduction tab therein when the tab is connected to a surgical implant. A retention element at least partially disposed within the instrument can be configured to engage the tab received in the opening so as to hold the tab securely within the instrument. With the tab received in the opening and held by the retention element, the surgical instrument can be configured to be manipulated to break the tab off the surgical implant. The broken tab can be retained within the surgical instrument by being held therein by the retention element. The instrument can be repeatedly relocated and repeatedly break off surgical reduction tabs of one or more surgical implants, with each successive tab received in the opening displacing the immediately preceding broken tab from the retention element such that a chamber formed (Continued)

in the instrument can simultaneously hold a plurality of broken tabs within the instrument.

20 Claims, 29 Drawing Sheets

Related U.S. Application Data

(60) Provisional application No. 61/706,860, filed on Sep. 28, 2012.

(58) Field of Classification Search
USPC .......................................... 606/86 A, 300–321
See application file for complete search history.

(56) References Cited

U.S. PATENT DOCUMENTS

| | | | | |
|---|---|---|---|---|
| 5,624,216 A * | 4/1997 | Detable | ............... | B25B 23/1415 411/3 |
| 5,928,236 A * | 7/1999 | Augagneur | ........ | A61B 17/8605 411/405 |
| 5,971,987 A * | 10/1999 | Huxel | ................ | A61B 17/8605 411/2 |
| 6,672,791 B2 * | 1/2004 | Schubring | ............. | F16B 5/0275 403/296 |
| 6,755,829 B1 | 6/2004 | Bono et al. | | |
| 7,666,189 B2 * | 2/2010 | Gerber | ............... | A61B 17/7074 606/104 |
| 7,846,167 B2 * | 12/2010 | Garcia | ................ | A61B 17/862 606/104 |
| 8,382,810 B2 * | 2/2013 | Peterson | .............. | A61B 17/862 411/2 |
| 8,435,305 B2 * | 5/2013 | Lozier | .................. | A61F 2/4601 606/86 R |
| 8,753,406 B2 * | 6/2014 | Lozier | .................. | A61F 2/4601 606/99 |
| 9,066,758 B2 * | 6/2015 | Justis | ................ | A61B 17/7032 |
| 9,149,308 B2 * | 10/2015 | Biedermann | ...... | A61B 17/7091 |
| 9,402,673 B2 | 8/2016 | Cormier et al. | | |
| 2003/0199872 A1 * | 10/2003 | Markworth | ........ | A61B 17/7086 606/86 A |
| 2006/0074418 A1 * | 4/2006 | Jackson | ............. | A61B 17/7086 606/914 |
| 2006/0074445 A1 * | 4/2006 | Gerber | ............... | A61B 17/7074 606/191 |
| 2006/0264962 A1 * | 11/2006 | Chin | .................. | A61B 17/7037 606/90 |
| 2007/0106283 A1 * | 5/2007 | Garcia | ................ | A61B 17/862 606/1 |
| 2007/0149982 A1 * | 6/2007 | Lyons | ................ | A61B 17/1604 606/99 |
| 2007/0288002 A1 * | 12/2007 | Carls | .................. | A61B 17/7032 606/86 A |
| 2008/0119849 A1 * | 5/2008 | Beardsley | .......... | A61B 17/7032 606/306 |
| 2008/0119850 A1 * | 5/2008 | Sicvol | ................ | A61B 17/7032 606/306 |
| 2008/0255576 A1 * | 10/2008 | Protopsaltis | ....... | A61B 17/7091 606/104 |
| 2008/0300638 A1 * | 12/2008 | Beardsley | .......... | A61B 17/7032 606/306 |
| 2008/0312693 A1 | 12/2008 | Trautwein et al. | | |
| 2009/0005822 A1 * | 1/2009 | Kitchens | ............ | A61B 17/1725 606/86 B |
| 2009/0105712 A1 * | 4/2009 | Dauster | .............. | A61B 17/7086 606/99 |
| 2009/0105718 A1 * | 4/2009 | Zhang | ................ | A61B 17/8863 606/104 |
| 2009/0149889 A1 * | 6/2009 | Peterson | .............. | A61B 17/862 606/305 |
| 2009/0171391 A1 * | 7/2009 | Hutton | ............... | A61B 17/7032 606/246 |
| 2009/0228051 A1 * | 9/2009 | Kolb | .................. | A61B 17/7032 606/305 |
| 2009/0306671 A1 * | 12/2009 | McCormack | ........ | A61B 17/025 606/90 |
| 2010/0036443 A1 * | 2/2010 | Hutton | ............... | A61B 17/7032 606/86 R |
| 2010/0331899 A1 * | 12/2010 | Garcia | ................ | A61B 17/865 606/308 |
| 2011/0009872 A1 * | 1/2011 | Mistry | .................. | A61F 2/4603 606/99 |
| 2011/0040335 A1 * | 2/2011 | Stihl | .................... | A61B 17/7032 606/302 |
| 2011/0184469 A1 * | 7/2011 | Ballard | ............... | A61B 17/7091 606/279 |
| 2011/0263945 A1 * | 10/2011 | Peterson | ............ | A61B 17/7074 600/213 |
| 2012/0053642 A1 * | 3/2012 | Lozier | ................... | A61F 2/4601 606/86 R |
| 2013/0245705 A1 * | 9/2013 | McBride | ............ | A61B 17/7032 606/86 R |
| 2013/0289633 A1 * | 10/2013 | Gleeson | ............... | A61B 17/708 606/86 A |
| 2013/0304217 A1 * | 11/2013 | Recber | .................. | A61F 2/2875 623/17.19 |
| 2014/0052180 A1 * | 2/2014 | Justis | ................ | A61B 17/7082 606/246 |
| 2014/0094862 A1 * | 4/2014 | Cormier | ............ | A61B 17/8863 606/86 R |
| 2014/0180298 A1 * | 6/2014 | Stevenson | .......... | A61B 17/7082 606/104 |
| 2014/0276896 A1 * | 9/2014 | Harper | ............... | A61B 17/7086 606/104 |

OTHER PUBLICATIONS

International Search Report and Written Opinion for Application No. PCT/US2013/060331 mailed Dec. 16, 2013 (16 Pages).

* cited by examiner

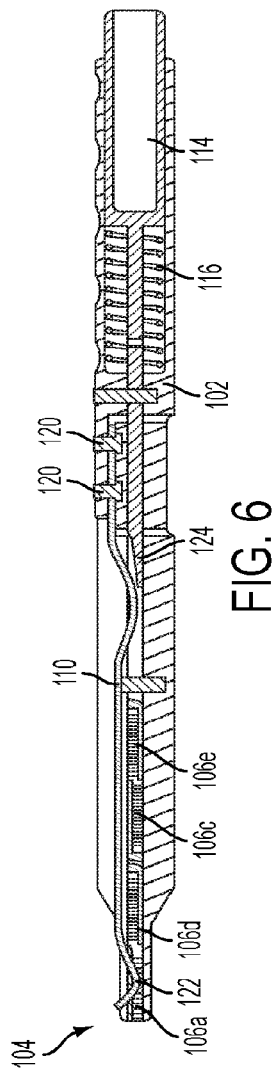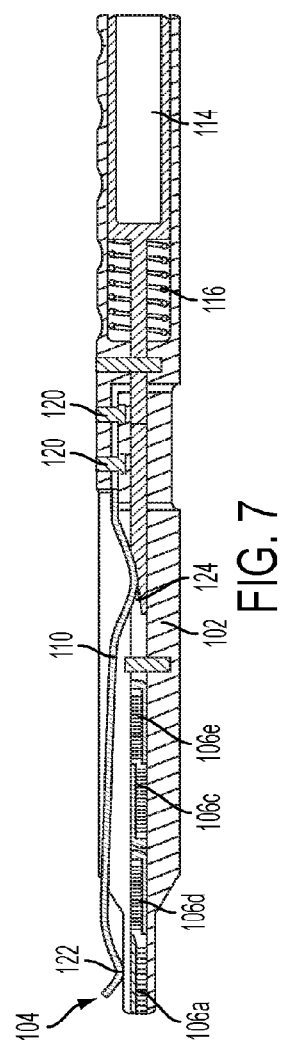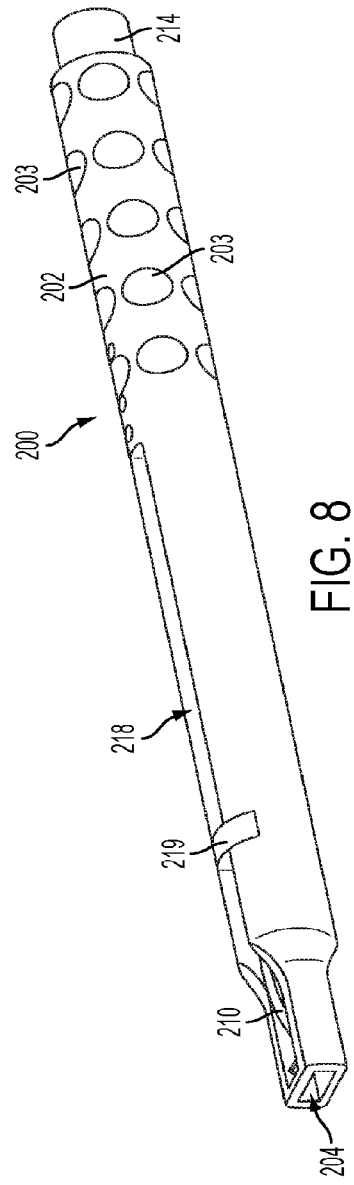

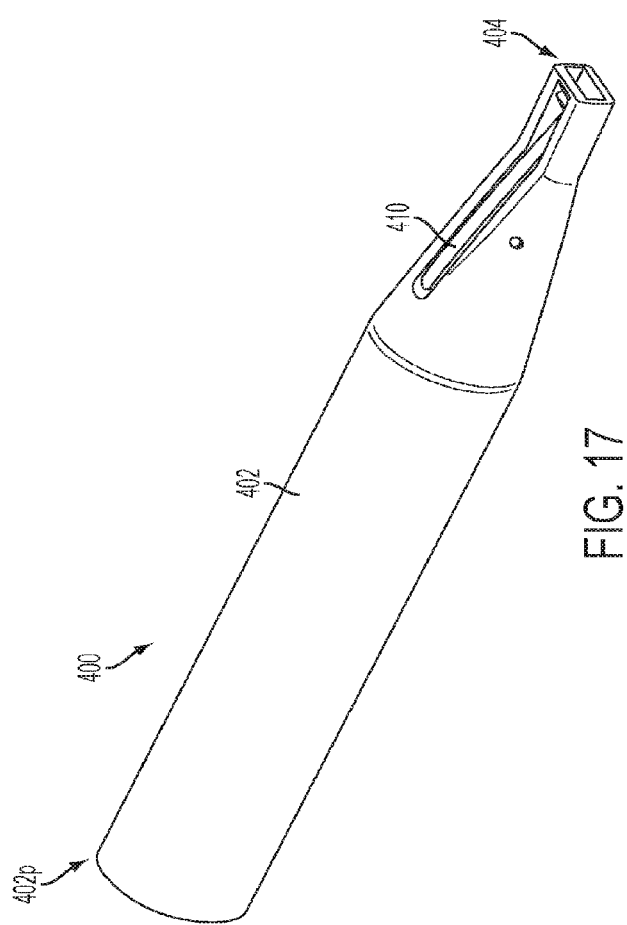
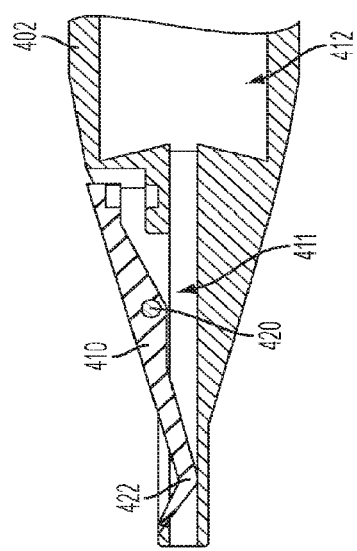
FIG. 17
FIG. 18

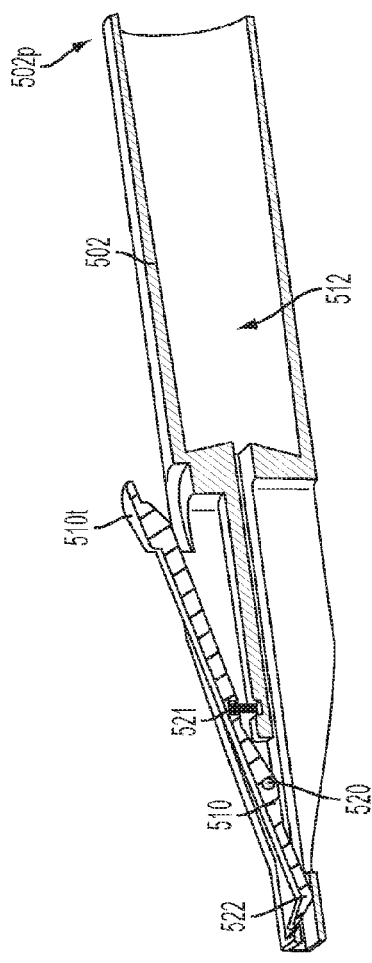
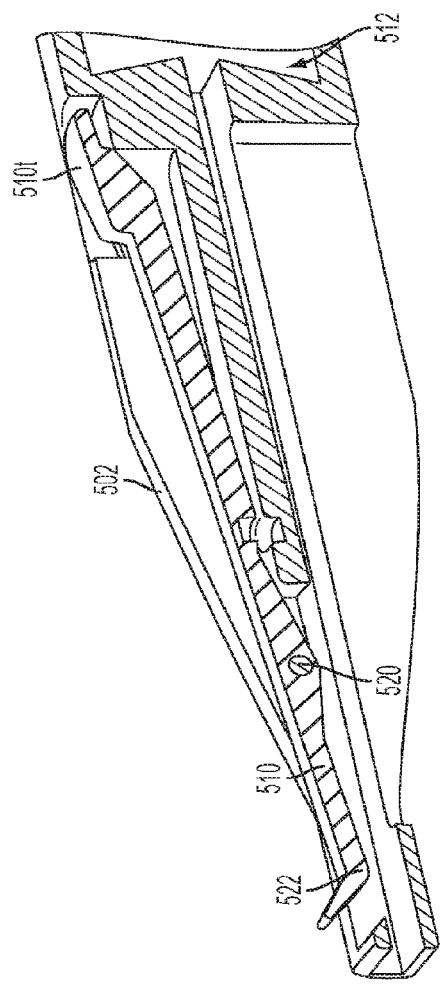
FIG. 21
FIG. 22

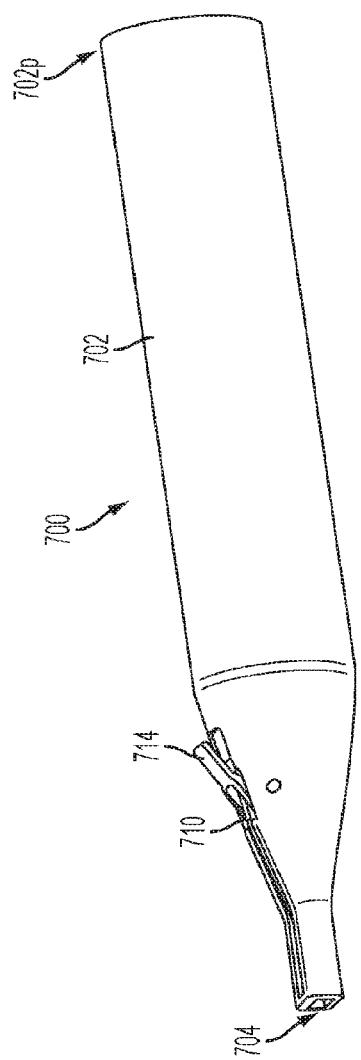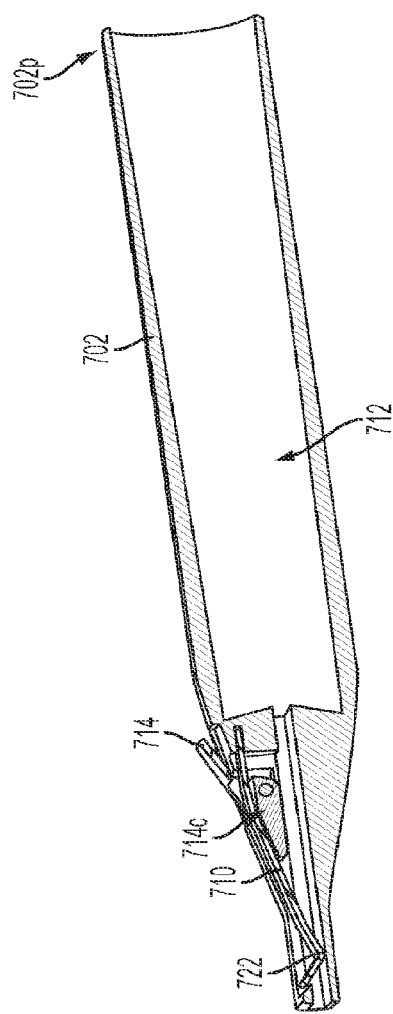
FIG. 30
FIG. 31

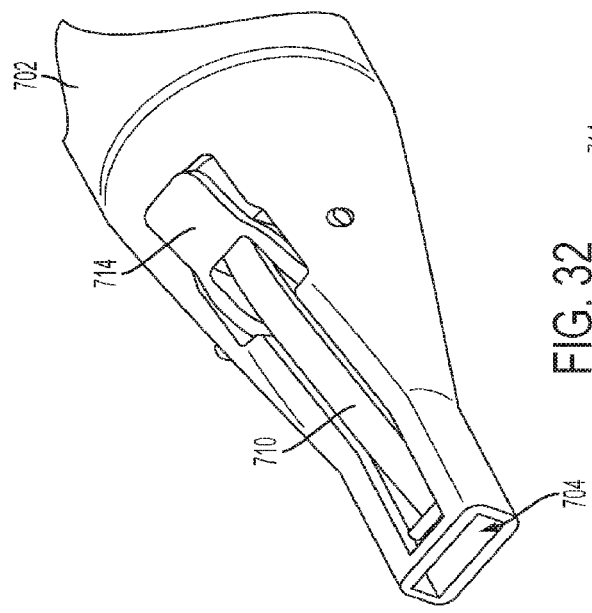
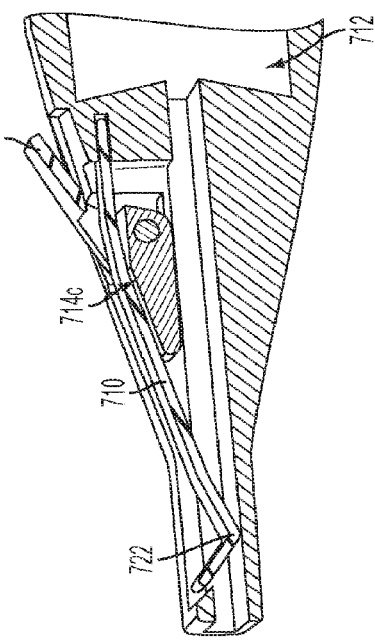
FIG. 32
FIG. 33

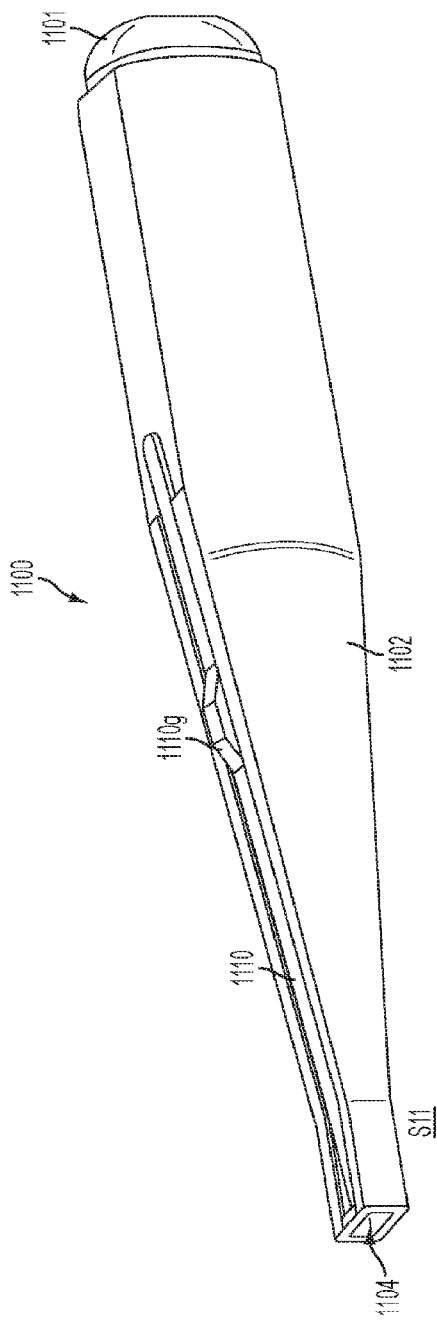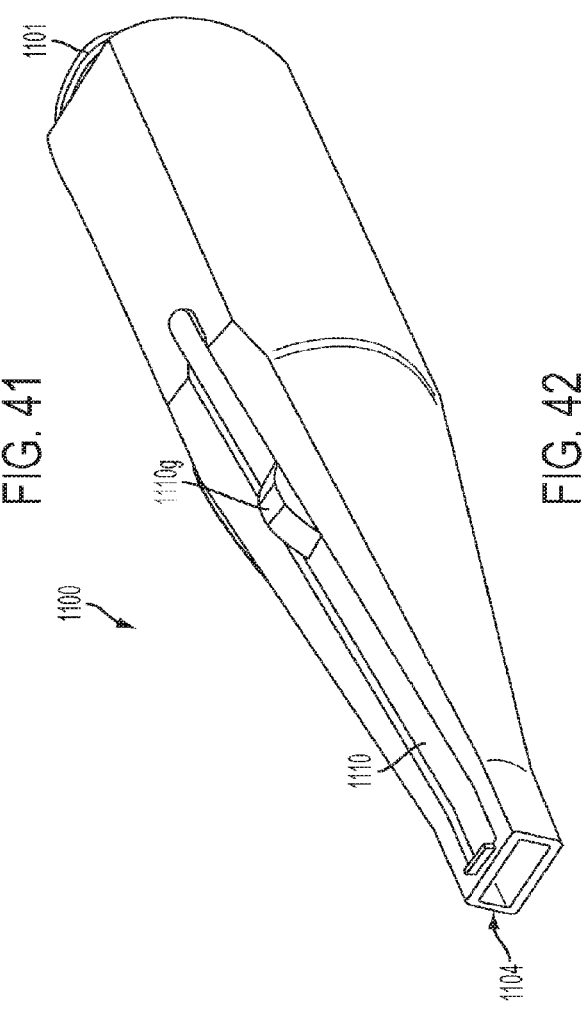

DEVICES AND METHODS FOR BREAKING AND RETAINING SURGICAL REDUCTION TABS

CROSS REFERENCE TO RELATED APPLICATIONS

The present application is a continuation of U.S. application Ser. No. 14/021,203 filed on Sep. 9, 2013, which claims priority to U.S. Provisional Application No. 61/706,860 entitled "Devices And Methods For Breaking And Retaining Surgical Reduction Tabs" filed on Sep. 28, 2012, each of which is hereby incorporated by reference in its entirety.

FIELD

The present disclosure relates generally to devices and methods for breaking and retaining surgical reduction tabs.

BACKGROUND

Some types of conventional surgical implants can have one or more reduction tabs extending therefrom. Conventional spinal anchors, for non-limiting example, typically have two opposed reduction tabs extending proximally therefrom. The reduction tabs of a surgical implant can be used in implanting the surgical implant, and then the reduction tabs can be broken off the implanted surgical implant to reduce a clearance height of the surgical implant, which can help prevent the surgical implant from damaging tissue and/or other material adjacent to the implant.

However, conventional devices used to break reduction tabs can only be used to break a small number of reduction tabs, typically one or two, before the device must be reoriented so that an opposite end of the device can be used and/or be removed from a patient and cleared of the broken tab(s) to break off another small number of reduction tabs, typically one or two. It can therefore take a significant amount of time to break all reduction tabs that need to be broken in a surgical procedure, as tens of reductions tabs can be needed to be broken in a single surgical procedure.

Some conventional devices used to break reduction tabs off of an implanted implant cannot retain the broken reduction tabs within the device, thereby leaving broken reduction tabs loose within the patient that need to be removed from the patient prior to ending the surgical procedure. Conventional broken reduction tabs are relatively small, which can make them difficult to retrieve in a patient. Further, since numerous reduction tabs may be broken in a single surgical procedure, it can take a significant amount of time to retrieve all of the loose broken reduction tabs. While some conventional devices used to break reduction tabs off of an implanted implant can retain the broken reduction tabs within the device, only a small number of broken reduction tabs, e.g., four or less or two or less, can be retained within the device before the device has to be replaced during a surgical procedure with another device to break and retain more reduction tabs and/or the device has to be removed from the patient and unloaded of broken tabs before being used to break more reduction tabs. It can therefore take a significant amount of time to break all reduction tabs that need to be broken in a surgical procedure, as tens of reductions tabs can be needed to be broken in a single surgical procedure.

Accordingly, there remains a need for devices and methods for breaking and retaining surgical reduction tabs.

SUMMARY

The present invention generally provides devices and methods for breaking and retaining surgical reduction tabs.

In one aspect, a surgical apparatus is provided that in one embodiment includes an elongate shaft and a retention element disposed at least partially within the shaft. The shaft can have proximal and distal ends, an opening at the distal end of the shaft, and a chamber formed therein proximal to and in communication with the opening. The distal end of the shaft can be configured to be advanced into a body of a patient, and the opening can be configured to receive a reduction tab of a surgical implant. The retention element can be located adjacent the opening and can be configured to hold the retention tab received in the opening in a fixed position relative to the shaft. The shaft can be configured to be manipulated to break the retention tab received in the opening and held by the retention element off from the surgical implant, and the chamber can be configured have the broken reduction tab disposed therein.

The plurality of broken reduction tabs can vary in number. For example, the plurality of broken reduction tabs can be at least five tabs. For example, the plurality of broken reduction tabs can be in a range of five to fifty tabs.

The chamber can be configured to have a plurality of broken reduction tabs simultaneously disposed therein.

The opening can be configured to sequentially receive the reduction tab and a plurality of additional reduction tabs of one or more surgical implants. The retention element can be configured to sequentially hold the reduction tab and each of the plurality of additional reduction tabs in a fixed position relative to the shaft. The shaft can be configured to be manipulated to break each of the plurality of additional retention tabs received in the opening and held by the retention element off of the one or more surgical implants. The chamber can be configured have the reduction tab and each of the broken additional reduction tabs simultaneously disposed therein. A first one of the plurality of reduction tabs can be configured to move the broken reduction tab from the fixed position and into the chamber. Each of a remainder of the plurality of reduction tabs can be configured to move an immediately preceding broken one of the reduction tabs from the fixed position and into the chamber. A first one of the plurality of reduction tabs can be configured to move the broken reduction tab proximally within the shaft. Each of a remainder of the plurality of reduction tabs can be configured to move an immediately preceding broken one of the reduction tabs proximally within the shaft. The plurality of broken reduction tabs can be at least five tabs and/or can be a range of five to fifty tabs.

The retention element can have any number of variations. For example, the retention element can be spring loaded. For another example, the retention element can direct a force toward an interior sidewall of the shaft such that the retention tab received in the opening is held between the retention element and the interior sidewall of the shaft. For yet another example, the retention element can have a pinch point in a distal portion thereof. The pinch point can be disposed adjacent to and proximal to the opening and can be configured to directly contact the retention tab received in the opening so as to hold the retention tab received in the opening in the fixed position. The pinch point can be disposed between the opening and a distal-most end of the chamber. For another example, the retention element can be configured to move between a first configuration in which the retention element is in a first position relative to a longitudinal axis of the shaft and a second configuration in which the retention element is in a second position relative to the longitudinal axis of the shaft. The second position can be radially offset from the first position relative to the longitudinal axis. For still another example, the retention element can include a bar at least partially disposed within the shaft.

The shaft can have a proximal opening in a proximal portion thereof. The proximal opening can be in communication with the chamber such that any broken retention tabs held in the chamber can be released from the chamber through the proximal opening.

The surgical apparatus can include a release element coupled to the retention element. The release element can be configured to be actuated to cause any broken retention tabs of surgical implants held in the chamber to be released from the chamber through the opening.

The reduction tab of the surgical implant can include a reduction tab extending proximally from a head of a surgical screw having a shank extending distally from the head.

In another embodiment, a surgical apparatus is provided that includes an elongate shaft and a retention element. The shaft can have an opening at a distal end thereof and a chamber formed therein that is in communication with the opening. The opening can be configured to sequentially receive a plurality of breakable extension tabs of one or more surgical implants therein. The shaft can be configured to be manipulated to sequentially break each of the breakable extension tabs off the one or more surgical implants. The chamber can be configured to retain each of the breakable extension tabs therein after the breakable extension tabs have been broken off the one or more surgical implants by manipulating the shaft. The retention element can be disposed at least partially within the shaft and located adjacent the opening. The retention element can be configured to sequentially engage each of the breakable extension tabs received in the opening within the shaft before the shaft is manipulated to sequentially break each of the breakable extension tabs off the one or more surgical implants. The retention element can be configured to hold within the shaft each of the breakable extension tabs after having been broken off the one or more surgical implants by manipulating the shaft.

Each of the broken breakable extension tabs except a last one of the broken breakable extension tabs can be displaced from being held by the retention element by a subsequent one of the breakable extension tabs received in the opening so as to sequentially advance each of the broken breakable extension tabs except the last one of the broken breakable extension tabs into the chamber.

The chamber can be configured to have a plurality of breakable extension tabs simultaneously disposed therein. The plurality of broken breakable extension tabs can be at least five tabs and/or can be in a range of five to fifty tabs.

The opening can be configured to sequentially receive the breakable extension tab and a plurality of additional breakable extension tabs of one or more surgical implants. The retention element can be configured to sequentially hold the breakable extension tab and each of the plurality of additional breakable extension tabs in a fixed position relative to the shaft. The shaft can be configured to be manipulated to break each of the plurality of additional breakable extension tabs received in the opening and held by the retention element off of the one or more surgical implants. The chamber can be configured have the breakable extension tab and each of the broken additional breakable extension tabs simultaneously disposed therein. A first one of the plurality of breakable extension tabs can be configured to move the broken breakable extension tab from the fixed position and into the chamber, and each of a remainder of the plurality of breakable extension tabs can be configured to move an immediately preceding broken one of the breakable extension tabs from the fixed position and into the chamber. A first one of the plurality of breakable extension tabs can be configured to move the broken breakable extension tab proximally within the shaft, and each of a remainder of the plurality of reduction tabs being configured to move an immediately preceding broken one of the breakable extension tabs proximally within the shaft. The plurality of broken breakable extension tabs can be at least five tabs and/or can be in a range of five to fifty tabs.

The retention element can have any number of variations. For example, the retention element can be spring loaded. For another example, the retention element can direct a force toward an interior sidewall of the shaft such that the breakable extension tab received in the opening is held between the retention element and the interior sidewall of the shaft. For yet another example, the retention element can have a pinch point in a distal portion thereof. The pinch point can be configured to directly contact the breakable extension tab received in the opening so as to hold the breakable extension tab received in the opening in the fixed position. The pinch point can be disposed between the opening and a distal-most end of the chamber. For another example, the retention element can be configured to move between a first configuration in which the retention element is in a first position relative to a longitudinal axis of the shaft and a second configuration in which the retention element is in a second position relative to the longitudinal axis of the shaft. The second position can be radially offset from the first position relative to the longitudinal axis. For still another example, the retention element can include a bar at least partially disposed within the shaft.

The shaft can have a proximal opening in a proximal portion thereof. The proximal opening can be in communication with the chamber such that any broken breakable extension tabs of surgical implants held in the chamber can be released from the chamber through the proximal opening.

The apparatus can include a release element coupled to the retention element. The release element can be configured to be actuated to cause any broken breakable extension tabs held in the chamber to be released from the chamber through the opening.

The apparatus of claim 20, wherein the breakable extension tab of the surgical implant comprises a breakable extension tab extending proximally from a head of a surgical screw having a shank extending distally from the head.

In another aspect, a surgical kit is provided that includes a surgical apparatus, e.g., any of the surgical apparatuses described herein. In one embodiment, the kit can include a plurality of surgical implants each having at least one reduction tab configured to be disposed within an opening of a shaft of the apparatus, broken by manipulating the shaft, and simultaneously retained in a chamber of the apparatus.

In another aspect, a surgical method is provided that includes disposing a first reduction tab of a first surgical implant implanted within a patient within an opening at a distal end of an elongate shaft such that a retention element disposed at least partially within the shaft engages the first reduction tab, manipulating the shaft to break the first reduction tab disposed within the opening off of the first surgical implant, retaining the broken first reduction tab within the shaft by the retention element holding the broken first reduction tab in a fixed position relative to the shaft, disposing a second reduction tab of a second surgical implant implanted within the patient within the opening such that the retention element engages the second reduction tab, manipulating the shaft to break the second reduction tab disposed within the opening off of the second surgical implant, and retaining the broken second reduction tab within the shaft such that the broken first and second reduction tabs are simultaneously retained within the shaft.

The method can vary in any number of ways. For example, disposing the second reduction tab within the opening can move the broken first reduction tab from being held in the fixed position relative to the shaft to being disposed within a chamber formed in the shaft. For another example, disposing the second reduction tab within the opening can move the broken first reduction tab proximally within the shaft. For yet another example, disposing the second reduction tab within the opening can cause the broken first reduction tab to be loosely disposed within the chamber. For another example, the retention element can retain the broken first reduction tab within the shaft by applying a spring force thereto, and the retention element can retain the broken second reduction tab within the shaft by applying a spring force thereto. For still another example, the method can include sequentially disposing a plurality of additional reduction tabs of at least one additional surgical implant implanted within the patient within the opening such that the retention element sequentially engages each of the plurality of additional reduction tabs, manipulating the shaft to sequentially break each of the plurality of additional reduction tabs disposed within the opening off of the at least one additional surgical implant, and retaining each of the broken plurality of additional reduction tabs within the shaft such that the broken first and second reduction tabs and the broken plurality of additional reduction tabs are simultaneously retained within the shaft.

BRIEF DESCRIPTION OF DRAWINGS

This invention will be more fully understood from the following detailed description taken in conjunction with the accompanying drawings, in which:

FIG. 6 is a cross-sectional view of the instrument of FIG. 1 having the reduction tab disposed therein, the reduction tab having been broken off the implant;

FIG. 7 is another cross-sectional view of the instrument of FIG. 1 having the reduction tab disposed therein, the reduction tab having been broken off the implant;

FIG. 8 is a perspective view of another embodiment of a surgical instrument configured to break and retain surgical reduction tabs;

FIG. 17 is another perspective view of the instrument of FIG. 15;

FIG. 18 is a partial cross-sectional view of the instrument of FIG. 15;

FIG. 21 is a cross-sectional view of the instrument of FIG. 20;

FIG. 22 is a partial cross-sectional view of the instrument of FIG. 20;

FIG. 30 is a perspective view of another embodiment of a surgical instrument configured to break and retain surgical reduction tabs;

FIG. 31 is a cross-sectional view of the instrument of FIG. 30;

FIG. 32 is a partial perspective view of the instrument of FIG. 30;

FIG. 33 is a partial cross-sectional view of the instrument of FIG. 30;

FIG. 41 is a perspective view of still another embodiment of a surgical instrument configured to break and retain surgical reduction tabs;

FIG. 42 is another perspective view of the instrument of FIG. 41;

DETAILED DESCRIPTION

Figure 1:
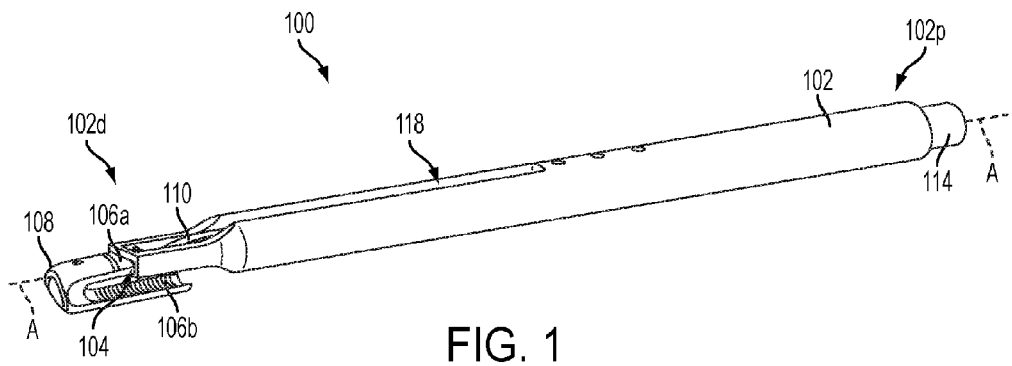
FIG. 1 is a perspective view of one embodiment of a surgical instrument configured to break and retain surgical reduction tabs, the instrument having a reduction tab attached to an implant inserted in an opening formed in a distal end of the instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various devices and methods are provided for breaking and retaining surgical reduction tabs. In general, the devices and methods can allow a single surgical instrument to break a plurality of surgical reduction tabs off one or more surgical implants and retain the broken tabs within the instrument. Surgical reduction tabs are also referred to herein as "breakable extension tabs."

In an exemplary embodiment, a surgical instrument can include an opening at a distal end thereof that is configured to receive a first surgical reduction tab therein when the first tab is connected to a surgical implant. A retention element at least partially disposed within the surgical instrument can be configured to engage the first tab received in the opening so as to hold the first tab securely within the instrument. With the first tab received in the opening and held by the retention element, the surgical instrument can be configured to be manipulated to break the first tab off the surgical implant, such as by rotating the surgical instrument and/or angling the surgical instrument relative to the surgical implant. The broken first tab can be retained within the surgical instrument by being held therein by the retention element. The surgical instrument can then be relocated, and a second surgical reduction tab of either the same surgical implant or a different surgical implant can be advanced into the opening at the instrument's distal end without the need to change the orientation of the surgical instrument. The second tab can displace the broken first tab from the retention element such that the broken first tab moves proximally within the instrument into a chamber formed in the surgical instrument, and the retention element can securely hold the second tab. The surgical instrument can be configured to be manipulated to break the second tab off its associated surgical implant, with the retention element holding the broken second tab so as to retain the broken second tab within the instrument already having the broken first tab retained therein. The instrument can be repeatedly relocated and repeatedly break off surgical reduction tabs of one or more surgical implants, with each successive tab received in the opening, e.g., on a same distal side of the instrument, displacing the immediately preceding broken tab from the retention element such that the chamber can simultaneously hold a plurality of broken tabs, e.g., up to fifty tabs, within the instrument.

The instrument can thus simultaneously retain a plurality of broken tabs therein, which can allow the instrument to break off multiple tabs without the instrument having to be removed from a patient's body to allow removal of broken tabs from the instrument before using the instrument to break off more tabs, which can save time since a single surgical procedure can include breaking off numerous tabs from one or more surgical implants. Also, since the instrument can be configured to receive each of the tabs in a same opening thereof, e.g., the distal end opening, the instrument need not be turned over or otherwise repositioned within a surgeon's hand during tab breaking, which can save time, since multiple tabs are typically successively broken near an end of a surgical procedure, and/or can be less cumbersome to use than instruments that must be turned over or repositioned within a surgeon's hand for the instrument to effectively break off multiple tabs.

The instrument can include a release mechanism configured to allow release of broken tabs retained therein from the instrument. The instrument can thus be configured to be reused with a same patient during a single surgical procedure if the instrument retains, or approaches retaining, a maximum number of broken tabs therein. The release mechanism can allow removal of the maximum number, or near maximum number, of broken tabs therefrom, thereby allowing the instrument to continue being used to break and retain tabs in the single surgical procedure, which can save time and can reduce a number of instruments used in the surgical procedure, which can reduce operating room clutter and/or reduce monetary cost. The instrument can also be configured to be reused with different patients in different surgical procedures by removing broken tabs therefrom using the release mechanism and then processing the instrument for reuse by cleaning, decontaminating, sterilizing, etc. the instrument in any one or more ways, as will be appreciated by a person skilled in the art.

Various types of surgical implants can include surgical reduction tabs, such as a head of a spinal anchor, e.g., a spinal screw, configured to seat a spinal fixation element, e.g., a spinal rod, therein. In the case of a spinal anchor, two surgical reduction tabs can extend proximally from opposed sides of a head of the spinal fastening member, and a spinal fastening member, e.g., a shank, can extend distally from the head. One embodiment of a spinal anchor including reduction tabs is the EXPEDIUM® Favored Angle Screw available from DePuy Synthes Spine, Inc. of Raynham, Mass. Various embodiments of spinal anchor assemblies including reduction tabs are further discussed in U.S. Pat. No. 6,755,829 entitled "Lock Cap Anchor Assembly For Orthopaedic Fixation" issued Jun. 29, 2004, which is hereby incorporated by reference in its entirety. However, as mentioned above, the surgical instruments disclosed herein can be used with any type of surgical implant that has one or more breakable extension tabs extending therefrom that are configured to be broken off the surgical implant, e.g., to be broken off after the surgical implant has been implanted in a patient's body and the tab(s) are no longer needed to facilitate implantation of the implant.

The surgical instruments disclosed herein can be formed of one or more materials. In an exemplary embodiment, the one or more materials are biocompatible so as to be safe for use in surgery. In an exemplary embodiment, the one or more materials can be rigid, e.g., stainless steel, titanium, etc., which can help the instrument break reduction tabs off surgical implants without the instrument itself breaking and without the instrument flexing so much while attempting to break a reduction tab that the instrument cannot exert enough force on the reduction tab to cause the reduction tab to break.

Figure 2:
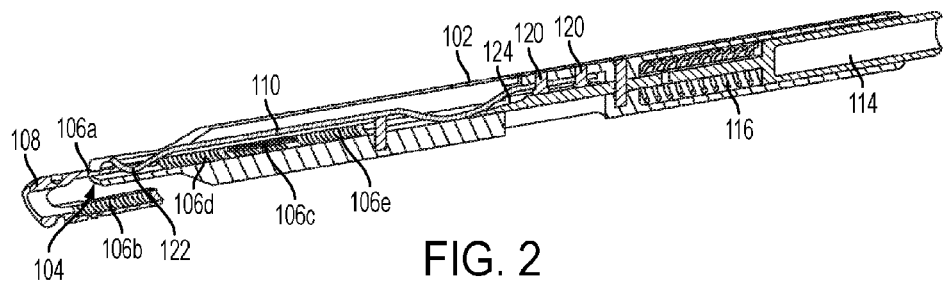
FIG. 2 is a cross-sectional view of the instrument of FIG. 1.
Figure 3:
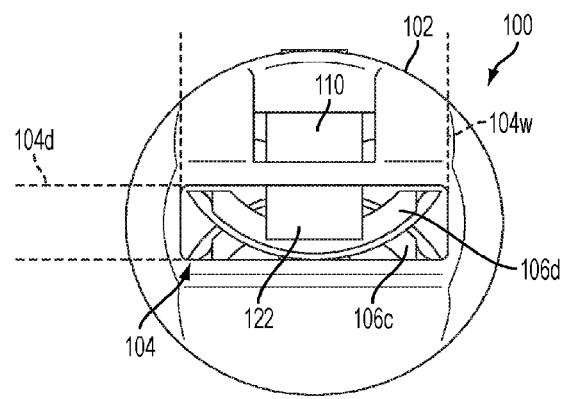
FIG. 3 is a distal end view of the instrument of FIG. 1.
Figure 4:
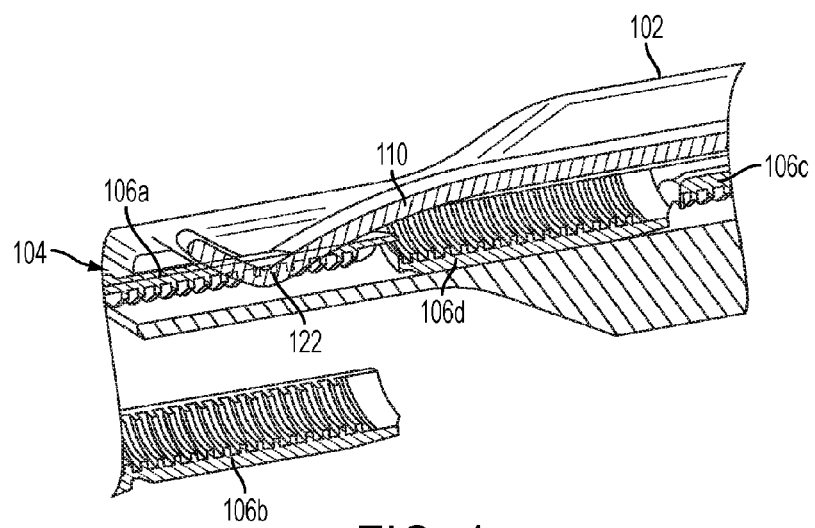
FIG. 4 is a partial cross-sectional view of the instrument of FIG. 1.
Figure 5:
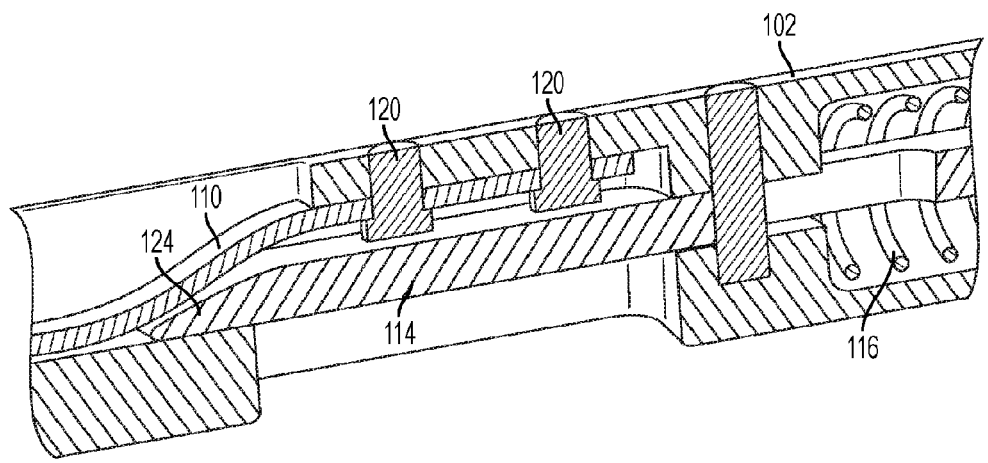
FIG. 5 is a another partial cross-sectional view of the instrument of FIG. 1.

FIGS. 1-7 illustrate an embodiment of a surgical instrument 100 configured to break and retain multiple reduction tabs of one or more surgical implants. As shown in FIGS. 1 and 2, the instrument 100 can include an elongate shaft 102 having a proximal end 102p and a distal end 102d. The shaft 102 can have an opening 104 formed at the distal end 102d thereof. The opening 104 can be configured to receive a first reduction tab 106a of a surgical implant therein. The opening 104 can also be configured to receive a second reduction 106b of the surgical implant therein, as discussed further below. FIGS. 1, 2, and 4 show the first reduction tab 106a received in the opening 104, while FIG. 3 shows the opening 104 without the first reduction tab 106a, the second reduction tab 106b, or any other reduction tab in the opening 104. The first and second reduction tabs 106a, 106b in the illustrated embodiment extend upwardly from a head 108 of a spinal anchor assembly. For ease of illustration, the spinal anchor assembly is only partially illustrated in FIGS. 1 and 2, e.g., a threaded polyaxial shank extending from the head 108 is not shown.

The shaft 102 can also include a retention element 110 at least partially disposed within the shaft 102. The retention element 110 can be disposed adjacent the opening 104 and can be configured to hold the first reduction tab 106a in a fixed position relative to the shaft 102 when the first reduction tab 106a is received in the opening 104. In other words, when the first reduction tab 106a is received in the opening 104, the retention element 110 can directly engage the reduction tab 106a so as to retain the first reduction tab 106a in place. The retention element 110 can thus be configured to facilitate breakage of the first reduction tab 106a from the surgical implant that includes the head 108 by helping to hold the first reduction tab 106a in a fixed position relative to the shaft 102 when the first reduction tab 106a is being broken via manual manipulation of the shaft 102. As shown in FIG. 2, the shaft 102 can also include a chamber 112 formed therein configured to hold broken reduction tabs therein at least after the first reduction tab 106a has been broken off the head 108. The retention element 110 can be configured to prevent broken reduction tabs from being released from the chamber 112 in cooperation with a release mechanism 114 of the instrument 100, as discussed further below.

The shaft 102 can have a variety of sizes, shapes, and configurations. The shaft 102 can generally have an elongate shape, which can facilitate insertion of at least a portion of the shaft 102 into a body of a patient. The shaft 102 in the illustrated embodiment has a cylindrical shape along a longitudinal length thereof in a proximal region of the shaft 102, although the proximal region of the shaft 102 can have a shape other than cylindrical. The cylindrical shape can facilitate smooth insertion of the shaft 102 through into a patient's body, either directly or through an introducer device such as a cannula. A person skilled in the art will appreciate that the proximal region of the shaft 102 may not be precisely cylindrical due to manufacturing tolerances but nevertheless be considered cylindrical. The proximal region of the shaft 102 can have a width that is greater than a width of a distal region of the shaft 102, which can facilitate retention of a plurality of broken retention tabs within the shaft 102 in the proximal region thereof, provide adequate space in the shaft 102 for the retention element 110 and/or the release mechanism 114, and/or facilitate secure holding of a reduction tab by the retention element 110 in the distal region of the shaft 102. The distal region of the shaft 102 can have a shape different than that of the proximal region, as in the illustrated embodiment in which the distal region has a rectangular box shape, or a same shape as the proximal region. The distal portion can have a shape other than as a rectangular box, but by having planar sides such as by having rectangular box shape, the distal portion can facilitate advancement of broken reduction tabs proximally within the shaft 102.

At least a portion of the shaft 102 can be configured to be advanced into a body of a patient. The portion of the shaft 102 configured to be so advanced can include at least the distal end 102d of the shaft 102 including the opening 104, thereby allowing the shaft 102 to facilitate breaking the reduction tab 106a off the implant after the implant has been implanted into the patient's body, e.g., after the shank of the implant has been threaded into bone.

The opening 104 at the distal end 102d of the shaft 102 can have a variety of sizes, shapes, and configurations. In an exemplary embodiment, the opening 104 can have a generally rectangular shape, as shown in FIG. 3, in which the opening 104 has a generally rectangular shape with rounded edges. By having a generally rectangular shape, the opening 104 can be configured to interchangeably receive reduction tabs therein having a concave side facing the retention element 110, such as the first retention tab 106a as shown in FIGS. 1, 2, 4, 6, and 7 and a third reduction tab 106c disposed within the chamber 112 as shown in FIGS. 2-4, 6, and 7, or having a convex side facing the retention element 110, such as a fourth reduction tab 106d and a fifth reduction tab 106e as shown in FIGS. 2-4, 6, and 7. Because a same surgical implant can include a plurality of reduction tabs with one or more of the tabs having a different orientation than one or more of the other tabs when the tabs are attached to the implant, such as the illustrated implant having reduction tabs 106a, 106b with facing concave surfaces, the opening 104 having a shape configured to interchangeably receive the differently oriented reduction tabs can allow the differently oriented reduction tabs to be received therein without having to rotate the opening 104 relative to the implant. The shaft 102 can thus be sequentially receive reduction tabs within the opening 104 without the shaft 102 needing to be turned over or otherwise repositioned within a surgeon's hand when successively breaking multiple tabs off one or more surgical implants, which can save time and/or make the instrument 100 easier to use in a small surgical space.

In another embodiment (not shown), an opening at a distal end of an elongate shaft can have an arc shape mimicking an arced cross-sectional shape of a reduction tab, such as the first, second, third, fourth, and fifth reduction tabs 106a, 106b, 106c, 106d, 106e which have arced cross-sections. The arced cross-sectional shape of the opening can help ensure that a particular side of a reduction tab inserted into the opening faces a retention element at least partially disposed within the shaft, which can facilitate secure holding of the tabs by the retention element, e.g., by having a convex surface of the tab protrude toward the retention element.

Referring again to the embodiment of FIGS. 1-7, the chamber 112 formed in the shaft 102 can have a variety of sizes, shapes, and configurations. The chamber 112 can have a width that is equal to or greater than a width 104w of the opening 104, shown in FIG. 3, and can have a depth that is equal to or greater than a depth 104d of the opening 104, also shown in FIG. 3, which can help ensure that reduction tabs inserted into the opening 104 can also fit into the chamber 112. The chamber 112 can thus have a width that is at least as large as a width of and can have a depth that is at least as large as a depth of reduction tabs configured to be received in the opening 104 and broken by the shaft 102. In the illustrated embodiment, the chamber 112 has a width equal to the width 104w of the opening 104 and a depth equal to the depth 104d of the opening 104.

A chamber formed in a shaft of a surgical instrument can be configured to allow broken reduction tabs to be loose therein or be non-loosely held therein. In the illustrated embodiment, the chamber 112 is configured to hold broken reduction tabs non-loosely therein with the broken reduction tabs being longitudinally aligned in a row, as shown in FIGS. 2-4, 6, and 7, in an orientation relative to the shaft 102 as the tabs were inserted into the opening 104, e.g., with a concave surface or convex surface thereof facing the retention element 110. In another embodiment, a chamber can be configured to otherwise non-loosely hold broken reduction tabs in another way, such as by stacking broken tabs one against another similar to a deck of cards. A chamber can be configured to loosely hold broken reduction tabs therein by allowing broken reduction tabs to be freely disposed therein in no particular order and/or in no particular orientation relative to the shaft, as discussed further below.

A chamber formed in a shaft of a surgical instrument can be formed in any portion of the shaft. In some embodiments, a chamber can extend through the shaft from a position proximal to an opening formed in a distal end of the shaft to a proximal end of the shaft. As in the illustrated embodiment, the chamber 112 can extend from a position to the opening 104 formed in the distal end 102d of the shaft 102 to a position distal to the proximal end 102p of the shaft 102, which can provide space within the shaft 102 for the release mechanism 114, discussed further below.

The retention element 110 can have a variety of sizes, shapes, and configurations. The retention element 110 can include a bar, as in the illustrated embodiment, although the retention element 110 can have other forms, such as a coiled spring. The retention element 110 can be at least partially disposed within the shaft 102, as in the illustrated embodiment in which a proximal portion of the retention element 110 is disposed within the shaft 102 and a distal portion of the retention element 110 is at least partially disposed outside the shaft 102.

The retention element 110 can be positioned at least partially within the shaft 102 so as to allow the retention element 110 to directly contact a reduction tab inserted into the opening 104, e.g., the first reduction tab 106a as shown in FIGS. 2, 4, and 6. The retention element 110 can thus be configured to directly contact at least a distal-most reduction tab disposed within the shaft 102. The retention element 110 can be configured to directly contact a reduction tab inserted into the opening 104 in a variety of ways. In an exemplary embodiment, the retention element 110 can include a distal portion thereof configured to direct a force toward one side of the shaft 102, e.g., toward one side of an interior sidewall of the shaft 102, such that the force can hold a reduction tab within the shaft 102 when the reduction tab is engaged by the force. The retention element 110 can be configured to direct the force in a variety of ways, such as by being spring loaded, as in the illustrated embodiment, such that the retention element 110 is biased toward the one side of the shaft 102. The retention element 110 can be spring loaded by, e.g., having a proximal end thereof attached to the shaft 102, e.g., using one or more pins 120, as shown in FIGS. 2 and 5-7, with a distal end of the retention element 110 being freely movable relative to the shaft 102. The force can be strong enough to hold the first reduction tab 106a in the shaft 102 but be weak enough that, after the first reduction tab 106a has been broken and is retained within the shaft by the retention element 110, a subsequent reduction tab, e.g., the second reduction tab 106b, inserted into the opening 104 can displace the first reduction tab 106a, e.g., push the first reduction tab 106a toward the chamber 112.

The retention element 110 can have a pinch point 122 in a distal portion thereof, as shown in FIGS. 2-4, 6, and 7. The pinch point 122 can be disposed adjacent to and proximal to the opening 104 and can be configured to directly contact the first retention tab 106a received in the opening 104 to hold the first retention tab 106a received in the opening 104 in a fixed position, both before and after the first reduction tab 106a has been broken from its associated implant, e.g., broken from the head 108. The force applied by the retention element 110 can thus be applied at the pinch point 122. The pinch point 122 can be disposed between the opening 104 and a distal-most end of the chamber 112. The retention tab 110 can thus be configured to hold the first reduction tab 106a before the retention tab 110 is fully disposed within the chamber 112, either loosely or non-loosely. A distance of the pinch point 122 from the opening 104 can be a distance less than a length of the first reduction tab 106a, which can allow the retention element 110 to directly contact the first reduction tab 106a at the pinch point 122 when the first reduction tab 106a in inserted into the opening 104. Reduction tabs of surgical implants have known lengths, so a pinch point of a retention element can be appropriately located in an instrument to directly contact reduction tabs.

As mentioned above, the instrument 100 can be configured to receive reduction tabs oriented in different ways relative to the opening 104 in which the tabs are sequentially received. The pinch point 122 of the retention element 110 can thus be configured to engage a concave side of a reduction tab to securely hold the reduction tab within the shaft 102, such as with the fourth and fifth reduction tabs 106d, 106e, and to engage a convex side of a reduction tab to securely hold the reduction tab within the shaft 102, such as with the first and third reduction tabs 106a, 106c.

The distal end of the retention element distal to the pinch point 122 can bend or curve away from the side of the shaft 102 to which the retention element 110 directs the force, as shown in FIGS. 2-4, 6, and 7. The bend or curve can help facilitate smooth insertion of the first reduction tab 106a into the opening 104 and help direct the first reduction tab 106a proximally into the shaft 102.

The retention element 110 can be configured to move between a first configuration in which the retention element 110 is in a first position relative to the longitudinal axis A of the shaft 102 and a second configuration in which the retention element 110 is in a second position relative to the longitudinal axis A of the shaft 102. The second configuration can be radially offset from the first configuration relative to the longitudinal axis A. The retention element 110 in the first configuration can be configured to hold the reduction tab 106a inserted into the opening 104 in a fixed position, and the retention element 110 in the second configuration can be configured to allow the reduction tab 106a inserted into the opening 104, as well as any reduction tabs disposed within the chamber 112, e.g., the third, fourth, and fifth tabs 106c, 106d, 106e, to be released from the shaft 102. The second configuration of the retention element 110 can thus be radially away from the side of the shaft 102 to which the retention element 110 is configured to direct the force, e.g., away from the interior sidewall of the shaft 102 against which the reduction tab 106a inserted into the opening 104 is held by the retention element 110.

The release mechanism 114 can have a variety of sizes, shapes, and configurations. The release mechanism 114 can include a selectively actuatable plunger, as in the illustrated embodiment, although the release mechanism 114 can have other forms, as discussed further below, such as a selectively actuatable lever and a movable end cap. The release mechanism 114 can be spring loaded, e.g., with the spring 116, as in the illustrated embodiment.

The release mechanism 114 can be at least partially disposed within the shaft 102, as in the illustrated embodiment in which a distal portion of the release mechanism 114 is disposed within the shaft 102 and a proximal portion of the release mechanism 114 is at least partially disposed outside the shaft 102, thereby allowing the proximal portion of the release mechanism 114 to be accessible by hand for manual actuation of the release mechanism 114. The release mechanism 114 can be positioned at least partially within the shaft 102 so as to allow the release mechanism 114 to directly contact a portion of the retention element 110 disposed with the shaft 102, as shown in FIG. 7. The release mechanism 114 can be actuated, e.g., by pushing distally on the proximal end of the release mechanism 114, thereby compressing the spring 116 and pushing a cam surface 124 of the release mechanism 114 distally against the retention element 110. The cam surface 124 can be at a distal end of the release mechanism 114. The cam surface 124 can include an angled cam surface, as in the illustrated embodiment as shown in FIGS. 2 and 5-7, which can facilitate camming of the retention element 110 by the release mechanism 114, as discussed further below.

Generally, the release mechanism 114 can be configured to be movable between a locked configuration and an unlocked configuration. In the locked configuration, shown in FIGS. 2, 5, and 6, the release mechanism 114 can be configured to retain broken tabs within the shaft 102 and to prevent release of retained broken tabs from the shaft 102. In the unlocked configuration, shown in FIG. 7, the release mechanism 114 can be configured to allow release of retained broken tabs from within the shaft 102. The release mechanism 114 can be configured in the unlocked configuration to allow release of retained broken tabs by pushing the cam surface 124 against the retention mechanism 110, thereby moving the pinch point 122 away from the side of the shaft 102 to which it is forced or biased. Any reduction tab held by the retention element 110 at the pinch point 122, e.g., the first reduction tab 106a, and any reduction tabs contained within the chamber 112, e.g., the third, fourth, and fifth tabs 106c, 106d, 106e, can be released from the shaft 102 through the opening 104, e.g., through gravity. The release mechanism 114 can thus be configured to allow the instrument 100 to be easily unloaded during a surgical procedure to free space within the chamber 112 for more broken tabs by allowing release of broken reduction tabs from within the shaft 102. The release mechanism 114 can also allow the instrument 100 to continue being used during a surgical procedure to break and retain reduction tabs even after the instrument 100 has broken and retained a maximum number of broken tabs that can be contained therein.

The release mechanism 114 can be biased to the locked configuration, thereby helping to prevent an accidental release of broken tabs from the instrument 100. In other words, a default position of the release mechanism 114 can be in the locked configuration. The release mechanism 114 can be biased to the locked configuration in a variety of ways. As in the illustrated embodiment, the release mechanism 114 can be spring-biased to the locked configuration with the spring 116. The spring 116 can be configured to provide a biasing force to the release mechanism 114 effective to hold the release mechanism 114 in the locked configuration, e.g., with the cam surface 124 not exerting a force against the retention element 110 so as to allow the pinch point 122 of the retention element 110 to directly contact the first reduction tab 106a inserted into the opening 104. Actuating the release mechanism 114 can move the release mechanism 114 between the locked configuration and the unlocked configuration.

As shown in FIG. 1, the shaft 102 can include a slot 118 formed therein that is configured to facilitate release of broken tabs from within the shaft 102. The slot 118 can be in communication with the chamber 112. The slot 118 can be configured to have a tool (not shown), e.g., a rod, a scalpel tip, etc., inserted therein and into the chamber 112. The slot 118 can be configured to allow a tool inserted therein to slide within the slot 118 to engage and push at least one broken tab within the chamber 112. The tool can be slid distally within the slot 118 to urge broken tab(s) within the chamber 112 out of the instrument 100 through the opening 104. The slot 118 can thus help broken tab(s) be quickly removed from within the shaft 102, help unjam any broken tab(s) within the shaft 102 in the unlikely event that the tab(s) become jammed therein, and/or help clear foreign material (e.g., tissue, blood, etc.) other than broken tab(s) from within the shaft 102. The tool can be slid within the slot 118 whether or not any broken tabs are within the chamber 112, which can facilitate clearing the chamber 112 of foreign material to, e.g., clear space for broken tabs to be disposed within the chamber 112.

Although the slot 118 can have a variety of configurations and positions in the shaft 102, in the illustrated embodiment, the slot 118 is a longitudinal slot extending parallel to a longitudinal axis A of the shaft 102 and extending between a distal point proximal to the distal end 102d of the shaft 102 and a proximal point distal to the proximal end 102p of the shaft 102. The proximal point can be adjacent to a proximal end of the chamber 112, which can facilitate pushing broken tabs within the chamber 112 distally using a tool inserted into the slot 118. The slot 118 can be formed on an opposite side to which the pinch point 122 is biased, as in the illustrated embodiment.

The first reduction tab 106a received in the opening 104 at the distal end 102d of the shaft 102 can be broken off its associated surgical implant in a variety of ways. In an exemplary embodiment, the shaft 102 can be configured to break the first reduction tab 106a by rotating about the longitudinal axis A of the shaft 102, e.g., by manual rotation of the shaft 102, and/or by angularly orienting the shaft 102 relative to the first reduction tab 106a, e.g., by manually tilting the shaft 102. The rotational force and/or torsional force applied by the shaft 102 to the first reduction tab 106a can cause the first reduction tab 106a to snap off its associated implant. The retention element 110 can engage and hold the first reduction tab 106a within the shaft 102 prior to breakage of the first reduction tab 106a, as discussed above, and the retention element 110 can accordingly retain and hold the first reduction tab 106a within the shaft 102 post-breakage. The first reduction tab 106a after being broken from its associated implant can thus be securely held within the shaft 102, e.g., cannot be released therefrom without actuating the release mechanism 114.

FIG. 6 illustrates the first reduction tab 106a disposed in the shaft 102 and held therein by the retention element 110 after being broken off the tab's associated surgical implant, e.g., snapped off the head 108 of the implant. From the locked configuration of FIG. 6, the release mechanism 114 can be actuated, e.g., the plunger can be pushed distally, as shown in FIG. 7, to move the release mechanism 114 to the unlocked configuration to allow the broken first reduction tab 106a and the broken reduction tabs 106c, 106d, 106e disposed in the chamber 112 to be released from the shaft 102.

Below are discussions of various other embodiments of surgical instruments configured to break and retain multiple reduction tabs of one or more surgical implants. The various embodiments discussed below can generally be configured and used similar to the surgical instrument 100 of FIGS. 1-7. Additionally, like-named elements and like-illustrated elements of the surgical instrument 100 and of the surgical instruments discussed below can be configured and used similar to one another.

Figure 9:
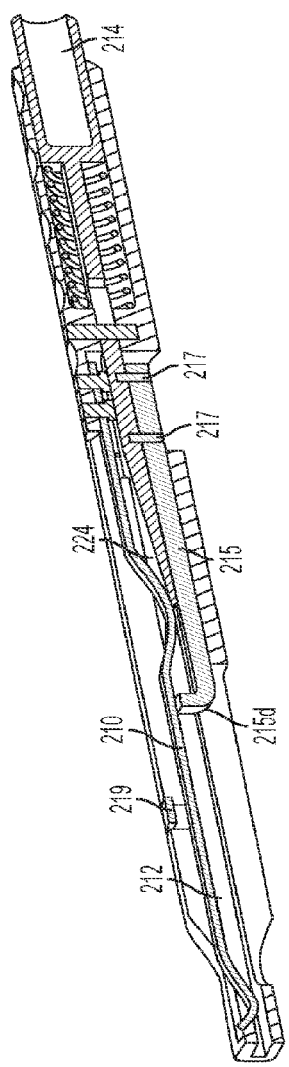
FIG. 9 is a cross-sectional view of the instrument of FIG. 8.
Figure 10:
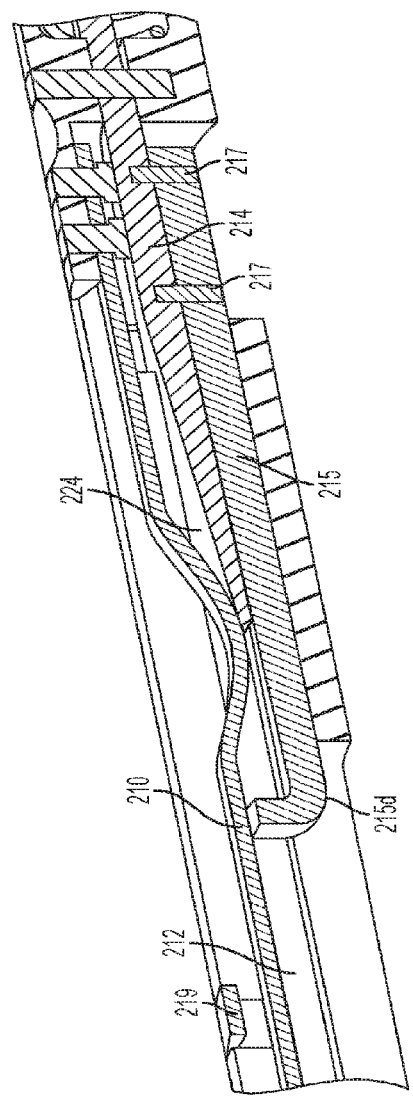
FIG. 10 is a partial cross-sectional view of the instrument of FIG. 8.
Figure 11:
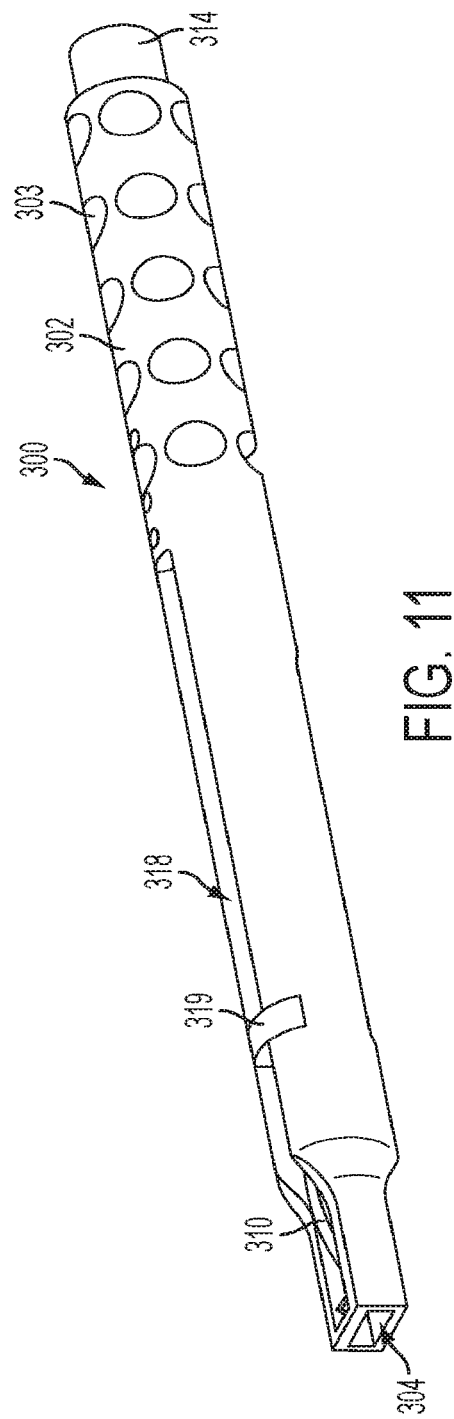
FIG. 11 is a perspective view of yet another embodiment of a surgical instrument configured to break and retain surgical reduction tabs.
Figure 12:
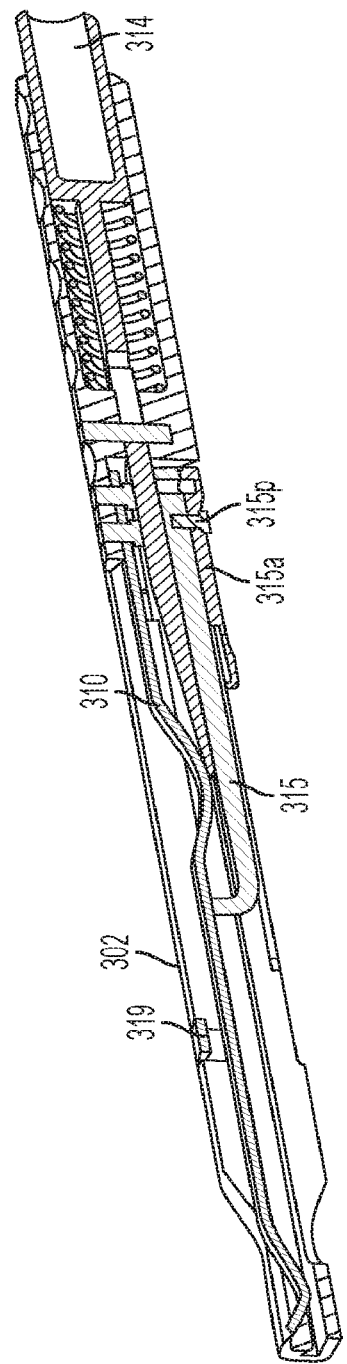
FIG. 12 is a cross-sectional view of the instrument of FIG. 11.
Figure 13:
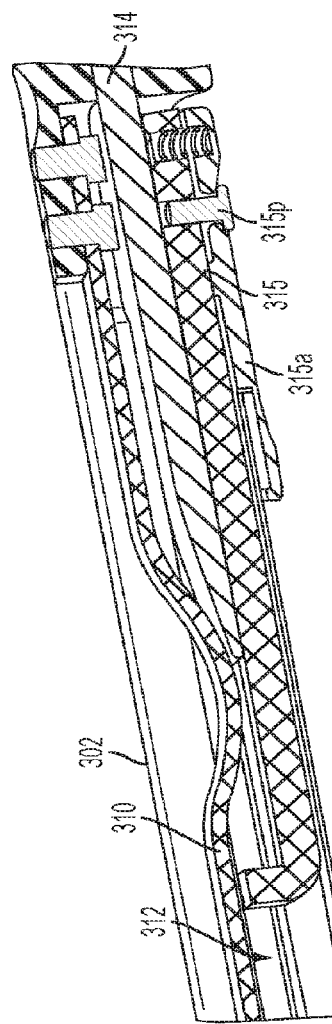
FIG. 13 is a partial cross-sectional view of the instrument of FIG. 11.
Figure 14:
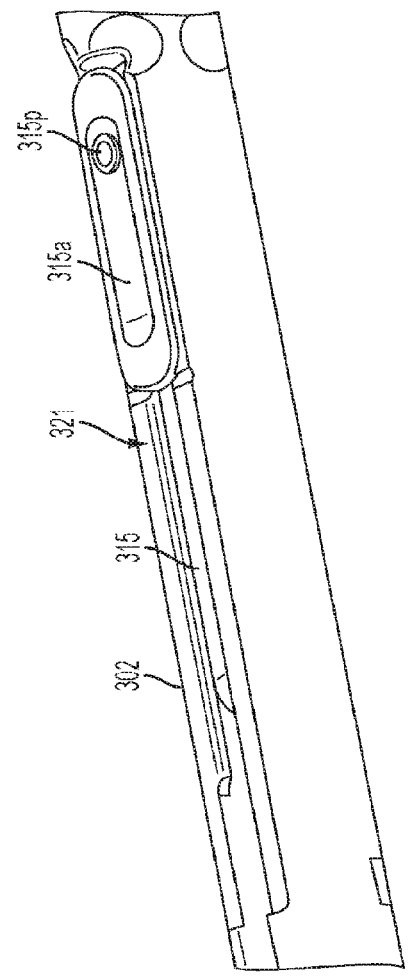
FIG. 14 is a partial perspective view of the instrument of FIG. 11.
Figure 15:
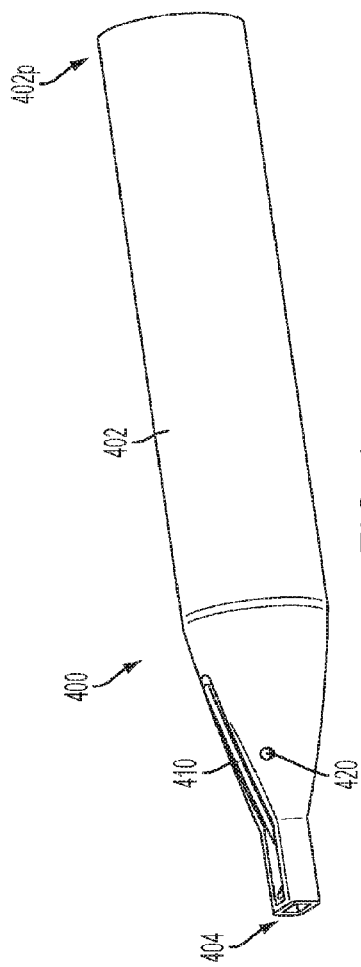
FIG. 15 is a perspective view of another embodiment of a surgical instrument configured to break and retain surgical reduction tabs.

FIGS. 8-10 illustrate another embodiment of a surgical instrument 200 configured to break and retain multiple reduction tabs of one or more surgical implants. The surgical instrument 200 includes a shaft 202 having an opening 204 at a distal end thereof, a retention element 210, a chamber 212 formed in the shaft 202, a release mechanism 214, and a longitudinal slot 218 formed in the shaft 202. An exterior surface of the shaft 202 can include one or more grip features configured to facilitate hand gripping of the shaft 202. The one or more grip features can help prevent the shaft 202 from slipping out of a surgeon's hand during insertion of tab(s) into the opening 204 and/or during breakage of reduction tab(s) using the shaft 202. Non-limiting examples of the one or more grip features can include a textured surface, finger hold(s), raised protrusion(s), and depression (s). In the illustrated embodiment, the one or more grip features include a plurality of depressions 203 formed in the shaft 202. The one or more grip features can be formed in at least a proximal portion of the shaft 202, e.g., in a portion of the shaft 202 most likely to be manipulated by hand during use.

As shown in FIGS. 9 and 10, the instrument 200 can include a jam release mechanism 215. The jam release mechanism 215 can have a variety of sizes, shapes, and configurations. The jam release mechanism 215 can include a bar, as in the illustrated embodiment, although the jam release mechanism 215 can have other forms, such as a coiled spring.

The jam release mechanism 215 can be configured to facilitate release of broken reduction tabs retained in the chamber 212. The jam release mechanism 215 can thus be configured to cooperate with the release mechanism 214 to release broken reduction tabs from the shaft 102. The jam release mechanism 215 can be attached to the release mechanism 214 such that the jam release mechanism 215 is configured to move in tandem with the release mechanism 214, e.g., when the release mechanism 214 moves between locked and unlocked configurations. The jam release mechanism 215 can be attached to the release mechanism 214 in a variety of ways, such as by using one or more pins 217. The jam release mechanism 215 can be configured to have a distal end 215d thereof positioned in the chamber 212 distal to a cam surface 224 of the release mechanism 214 such that the release mechanism 214 moving distally causes the distal end 215d of the jam release mechanism 215 to move distally in the chamber 212. The distal end 215d of the jam release mechanism 215 can thus be configured to distally push broken reduction tab(s) disposed in the chamber 212, facilitating release thereof through the opening 204. The jam release mechanism 215 can be positioned toward a side of the shaft 202 to which the retention element 210 is biased such that when the cam surface 224 of the release mechanism 214 urges the retention element 210 away from the side of the shaft 202, the jam release mechanism 215 does not get in the way of the retention element's movement, and vice versa.

As shown in FIGS. 8-10, the instrument 200 can include a stop element 219 configured to stop the retention element 210 from moving beyond a certain point when the release mechanism 214 is urging the retention element 210 away from the side of the shaft 202 to which the retention element 210 is biased. In this way, the retention element 210 can have movement thereof restrained to within a certain distance radially away from the shaft 202, which can help prevent the retention element 210 from interfering with other instruments and/or other material in a surgical space. The stop element 219 can have a variety of sizes, shapes, and configurations. As in the illustrated embodiment, the stop element 219 can include a bar spanning across the slot 218 in a distal portion of the slot 218.

FIGS. 11-14 illustrate another embodiment of a surgical instrument 300 configured to break and retain multiple reduction tabs of one or more surgical implants. The surgical instrument 300 includes a shaft 302 having an opening 304 at a distal end thereof, one or more grip features 303 on the shaft 302, a retention element 310, a chamber 312 formed in the shaft 302, a release mechanism 314, a jam release mechanism 315, a stop element 319, and a longitudinal slot 318 formed in the shaft 302. The jam release mechanism 315 in the illustrated embodiment is not attached to the release mechanism 314 so as to move in tandem therewith. Instead, the jam release mechanism 315 is configured to be movable independent of the release mechanism 314. In other words, the jam release mechanism 315 can be selectively actuated separate from the release mechanism 314 to facilitate removal of broken reduction tab(s) from within the shaft 302. The jam release mechanism 315 can be configured to be selectively actuated in a variety of ways. As in the illustrated embodiment, the jam release mechanism 315 can include an actuator 315a configured to be manipulated to move the jam release mechanism 315 relative to the shaft 302. The actuator 315a can be configured to be manually actuated, such as by sliding the actuator 315a longitudinally back and forth, e.g., proximally and distally, thereby allowing the jam release mechanism 315 to move back and forth within the chamber 312 to help unjam any jammed broken reduction tabs contained therein. The jam release mechanism 315 can include a post 315p coupled to the actuator 315a and configured to move within a second slot 321, shown in FIG. 14, formed in the shaft 302 to help guide the jam release mechanism 315 back and forth relative to the shaft 302.

FIGS. 15-19 illustrate another embodiment of a surgical instrument 400 configured to break and retain multiple reduction tabs of one or more surgical implants. The surgical instrument 400 includes a shaft 402 having an opening 404 at a distal end thereof, a retention element 410, and a chamber 412 formed in the shaft 402. The chamber 412 can be configured to loosely retain broken reduction tabs therein. The chamber 412 can extend along a majority of a longitudinal length of the shaft 402, which can help maximize a number of broken reduction tabs that can be simultaneously retained therein. To enter the chamber 412 so as to be loosely held therein, a broken reduction tab held by a pinch point 422 of the retention element 410 can be pushed proximally toward the chamber 412 by a reduction tab inserted into the opening 404 immediately subsequent to the broken reduction tab. Depending on the lengths of the broken reduction tab and the immediately subsequent reduction tab, the broken reduction tab may be pushed fully into the chamber 412 or may be pushed toward the chamber 412 in a channel 411, shown in FIGS. 16, 18, and 19, extending between and connecting the opening 404 and the chamber 412 without being fully disposed therein until another reduction tab is inserted into the opening 404.

Broken reduction tabs loosely disposed in the chamber 412 can be released from the shaft 402 by turning the shaft 402 and allowing the broken reduction tabs to slide out of an open proximal end 402p of the shaft 402. The shaft 402 can optionally include an end cap (not shown) at the proximal end 402p thereof that can serve as a release mechanism configured to retain the broken reduction tabs within the shaft 402 until actuation of the end cap, e.g., removal or opening thereof. The end cap can be attached to the shaft 402 and movable relative thereto in a variety of ways, e.g., mateable threads, a hinged connection similar to a flip-top lid, a magnetic connection, etc.

Figure 16:
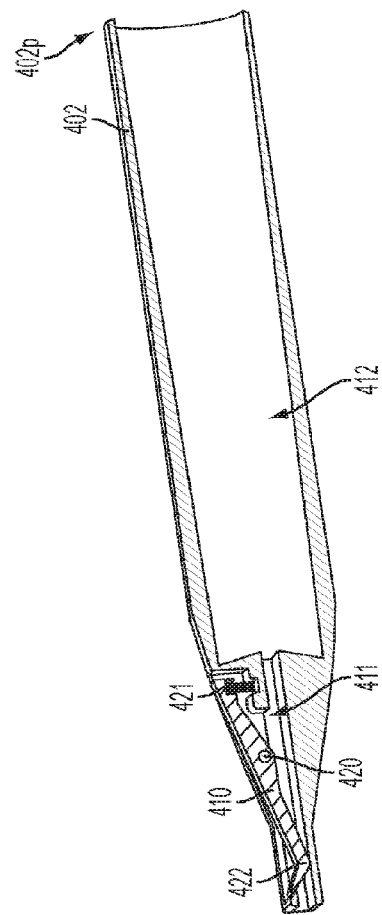
FIG. 16 is a cross-sectional view of the instrument of FIG. 15.
Figure 19:
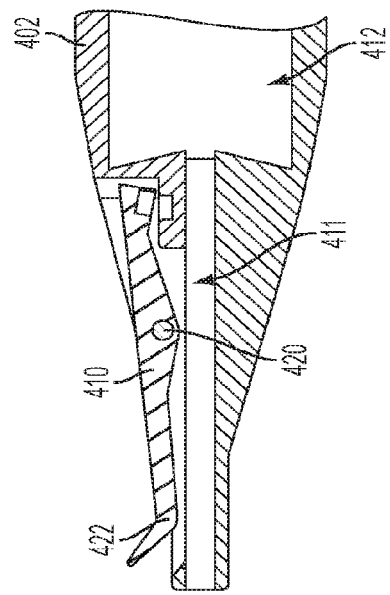
FIG. 19 is another partial cross-sectional view of the instrument of FIG. 15.

The retention element 410 can be spring loaded by, e.g., having a proximal end thereof attached to the shaft 402, e.g., using a spring 421, as shown in FIG. 16 (the spring 421 is not shown for clarity in FIGS. 18 and 19), and having an intermediate point thereof attached to the shaft 402 at a pivot point thereof, e.g., using a pin 420, as shown in FIGS. 15, 16, 18, and 19, such that the retention element 410 can pivot about the pin 420 as the spring 421 compresses and decompresses. FIGS. 15-18 illustrate the retention element 410 in a first configuration in which the retention element 410 can be configured to hold a reduction tab inserted into the opening 404 in a fixed position, and FIG. 19 illustrates the retention element 410 in a second configuration in which the retention element 410 can be configured to allow a reduction tab inserted into the opening 404, as well as any reduction tabs disposed within the chamber 412 to be released from the shaft 402 through the opening 404 and/or through the open proximal end 402p.

Figure 20:
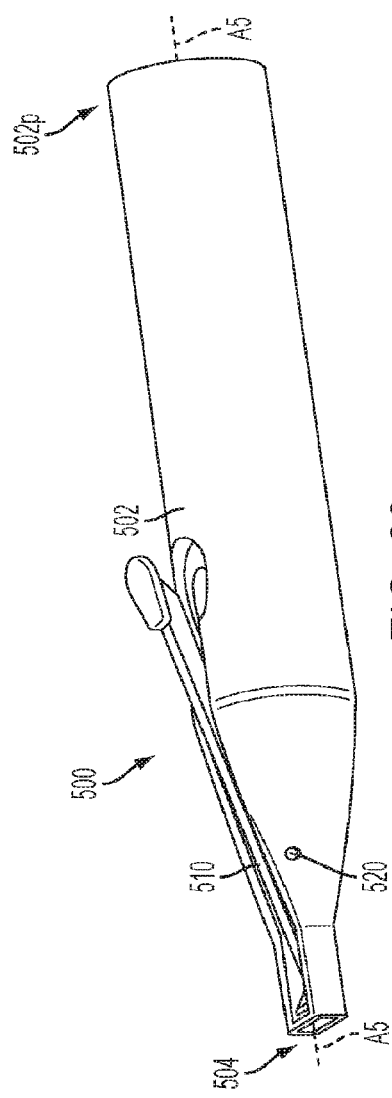
FIG. 20 is a perspective view of still another embodiment of a surgical instrument configured to break and retain surgical reduction tabs.
Figure 23:
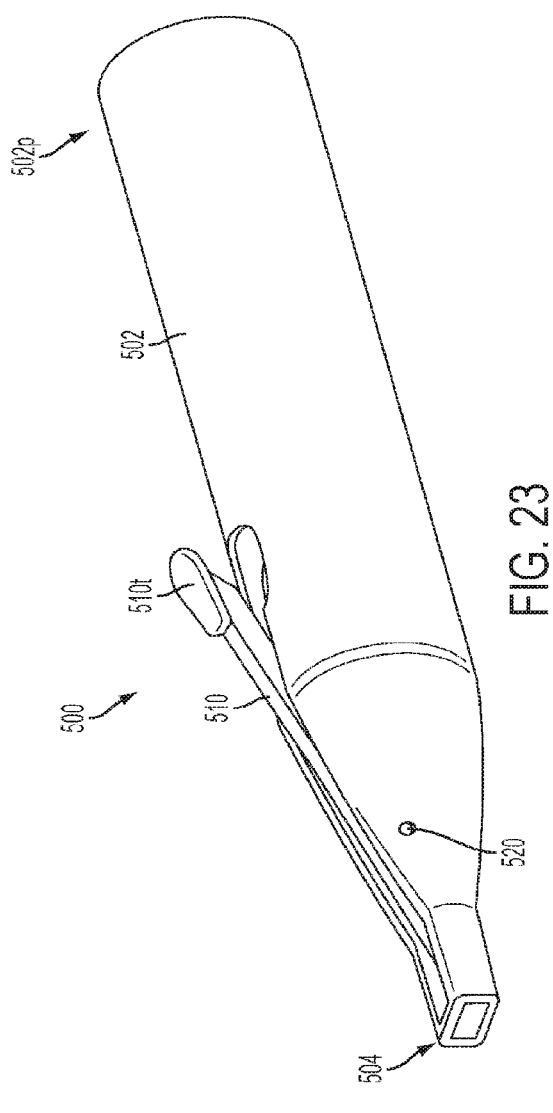
FIG. 23 is another perspective view of the instrument of FIG. 20.
Figure 24:
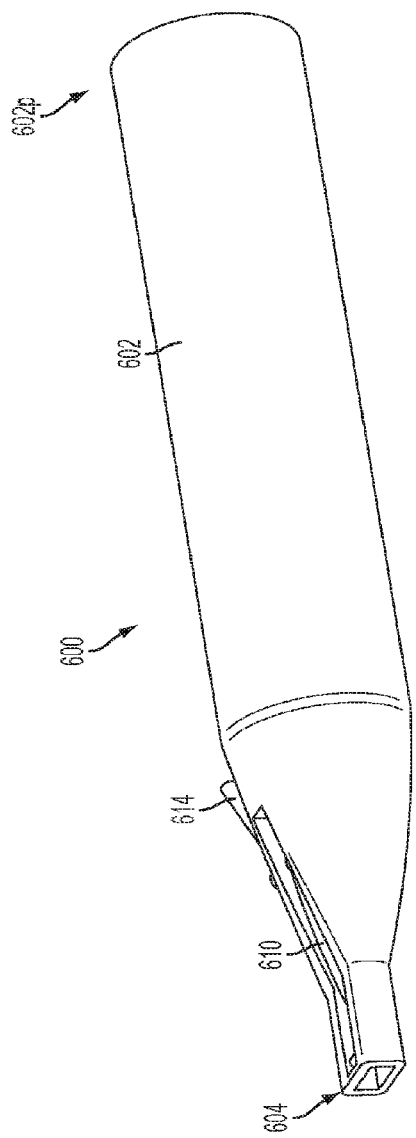
FIG. 24 is a perspective view of yet another embodiment of a surgical instrument configured to break and retain surgical reduction tabs.

FIGS. 20-23 illustrate another embodiment of a surgical instrument 500 configured to break and retain multiple reduction tabs of one or more surgical implants. The surgical instrument 500 includes a shaft 502 having an opening 504 at a distal end thereof, a retention element 510, and a chamber 512 formed in the shaft 502. The retention element 510 can be spring loaded and can be pivotable using a spring 521 (not shown in FIG. 22 for clarity of illustration) and a pivot pin 520, similar to the spring 421 and the pin 420 of the embodiment illustrated in FIGS. 15-19. The retention element 510 can be configured as a release mechanism of the instrument 500 by being configured to be selectively, manually movable between a first configuration in which the retention element 510 can be configured to hold a reduction tab inserted into the opening 504 in a fixed position, and a second configuration in which the retention element 510 can be configured to allow a reduction tab inserted into the opening 504, as well as any reduction tabs disposed within the chamber 512 to be released from the shaft 502 through the opening 504. Also, the retention element 510 in the second configuration can allow an unbroken reduction tab held by a pinch point 522 of the retention element 510 to be released from the instrument 500 through the opening 504. Similar to that discussed above regarding the instrument 100 of FIGS. 1-7, in the second configuration, the retention element 510 can be radially offset from the first configuration relative to a longitudinal axis A5 of the shaft 502 such that the pinch point 522 of the retention element 510 can be radially offset from its position in the first configuration relative to the longitudinal axis A5. FIGS. 20, 21, and 23 show the retention element 510 in the first configuration, and FIG. 22 shows the retention element 510 in the second configuration.

The retention element 510 can be configured to be selectively, manually movable between the first and second configurations in a variety of ways. In the illustrated embodiment, the retention element 510 includes a manually depressible tab 510t at a proximal end thereof. The manually depressible tab 510t can be selectively pushed down, e.g., radially inward, which can cause the retention element 510 to pivot about the pivot pin 520 and cause the pinch point 522 to move up, e.g., radially outward. Releasing the manually depressible tab 510t can allow the retention element 510 to pivot about the pivot pin 520 and cause the pinch point 522 to move down.

Similar to the chamber 412 of the embodiment illustrated in FIGS. 15-19, the chamber 512 can be configured to loosely retain broken retention tabs therein, and the shaft 502 can be configured to release broken retention tabs retained therein through an open proximal end 502p thereof and/or through the opening 504. The open proximal end 502p can optionally include an end cap (not shown) closing the proximal end 502p such that loose tabs in the chamber 512 cannot be released through the proximal end 502p without first releasing the end cap, e.g., flipping the end cap open, unthreading the end cap from the shaft 502, etc.

FIGS. 24-29 illustrate another embodiment of a surgical instrument 600 configured to break and retain multiple reduction tabs of one or more surgical implants. The surgical instrument 600 includes a shaft 602 having an opening 604 at a distal end thereof, a retention element 610, a chamber 612 formed in the shaft 602, and a release mechanism 614. The retention element 610 can be spring biased by having a proximal end thereof attached to the shaft 602 by compression fit as in the illustrated embodiment or in another way, e.g., using one or more pins (not shown), with a distal end of the retention element 610 being freely movable relative to the shaft 602.

Figure 25:
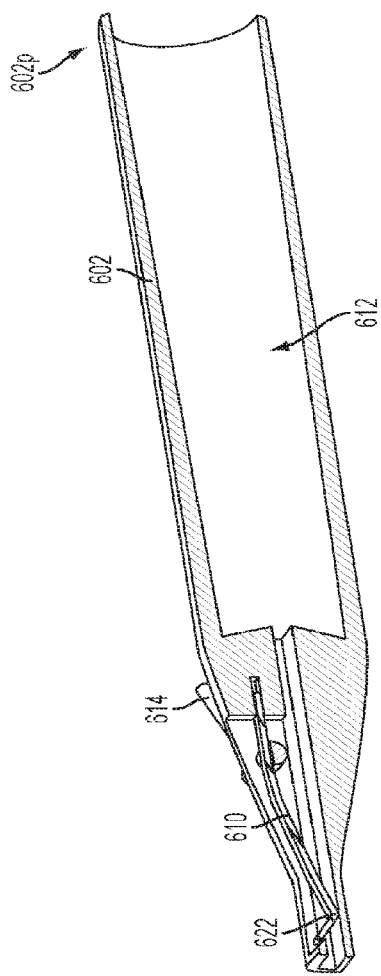
FIG. 25 is a cross-sectional view of the instrument of FIG. 24.
Figure 26:
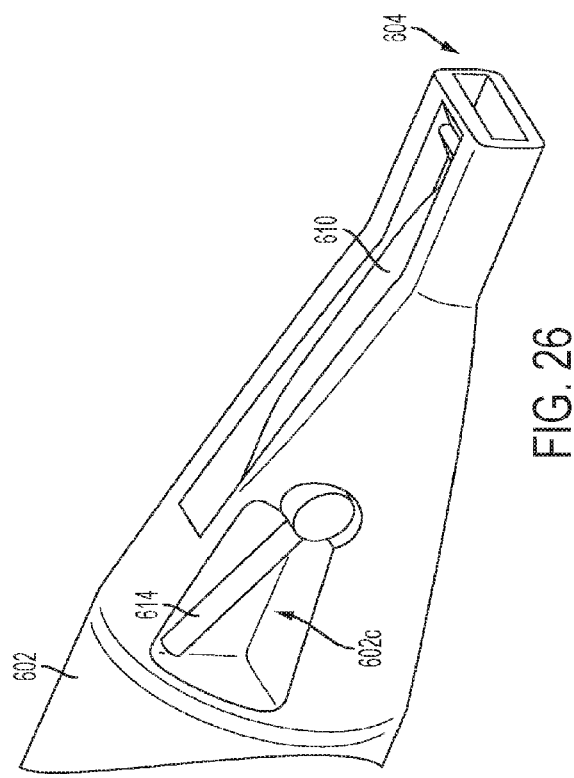
FIG. 26 is a partial perspective view of the instrument of FIG. 24.
Figure 27:
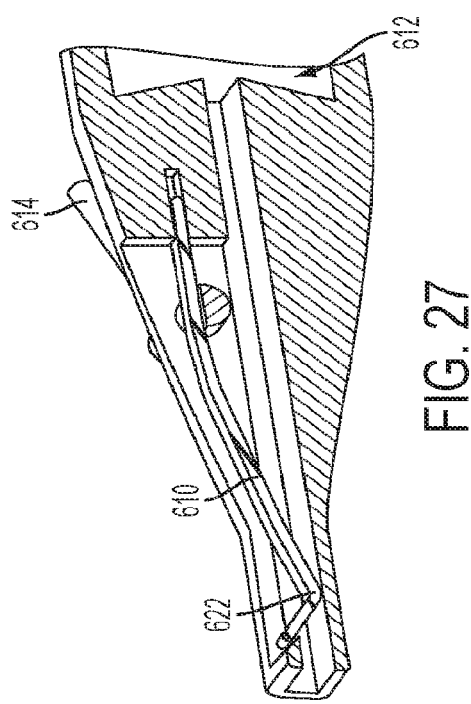
FIG. 27 is a partial cross-sectional view of the instrument of FIG. 24.
Figure 28:
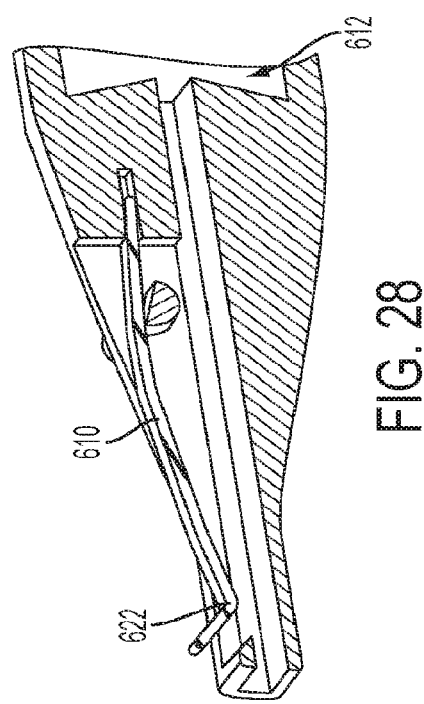
FIG. 28 is another partial cross-sectional view of the instrument of FIG. 24.
Figure 29:
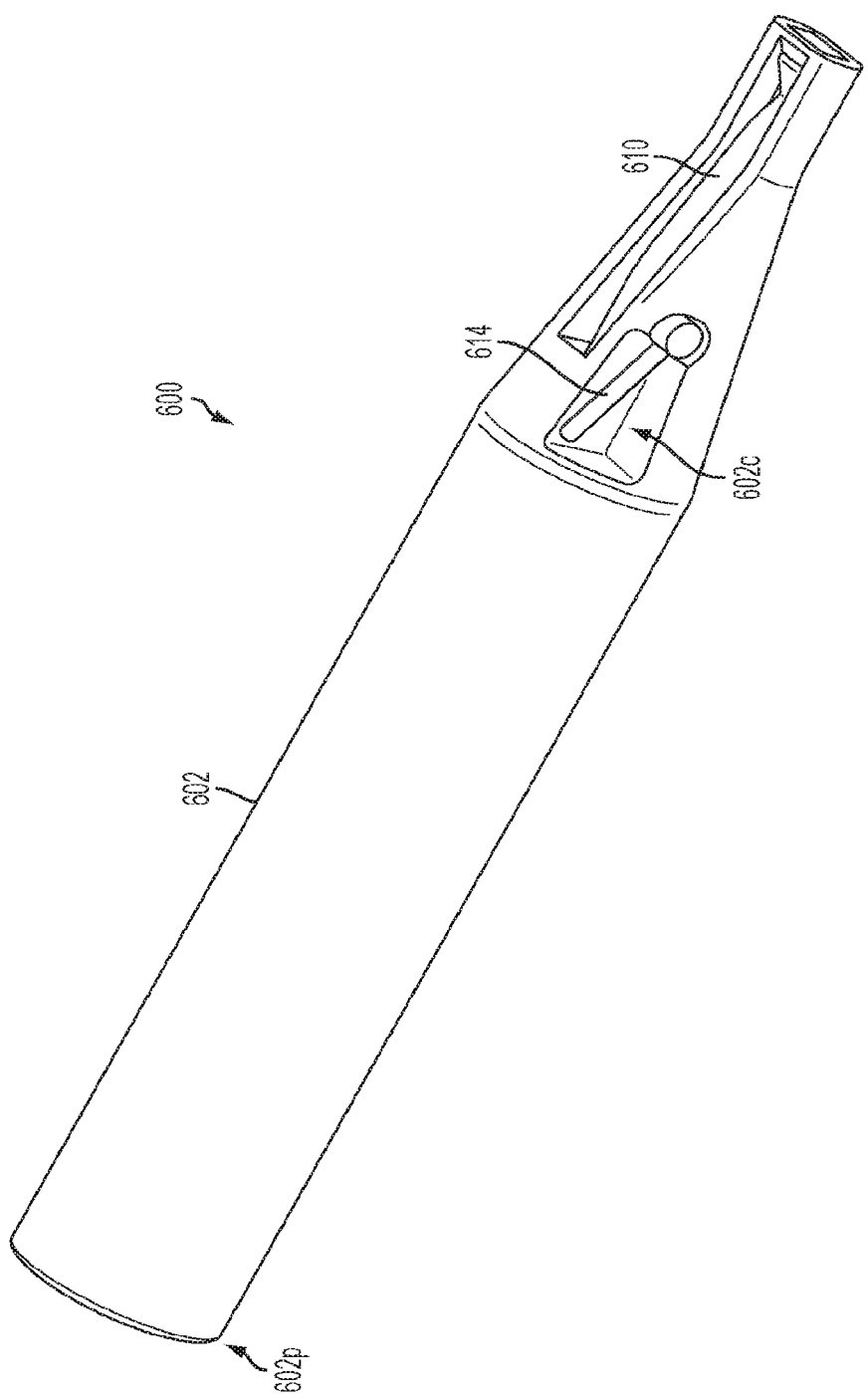
FIG. 29 is another perspective view of the instrument of FIG. 24.

The release mechanism 614 can include a lever configured to be selectively, manually actuatable to move the retention element 610 between first and second configurations to allow broken reduction tabs to be selectively released from the shaft 602 through the opening 604 and/or to allow an unbroken reduction tab held by a pinch point 622 of the retention element 610 to be released from the instrument 600 through the opening 604. The shaft 602 can include a recessed portion 602c, shown in FIGS. 26 and 29, formed therein that can be configured to seat the lever and allow movement of the lever therein, which can help prevent the lever from interfering with other materials, e.g., instruments, tissue, etc., in a surgical space. As shown in FIGS. 25, 27, and 28, the release mechanism 614 can include a cam 614c, e.g., at a distal end thereof, configured to engage the retention element 610 to move the retention element 610 between the first and second configurations. The cam 614c can be configured to rotate in response to manual actuation of the lever, thereby allowing the retention element 610 to pivot. FIGS. 24-27 and 29 show the retention element 610 in the first configuration, and FIG. 28 shows the retention element 610 in the second configuration.

Similar to the chamber 412 of the embodiment illustrated in FIGS. 15-19, the chamber 612 can be configured to loosely retain broken retention tabs therein, and the shaft 602 can be configured to release broken retention tabs retained therein through an open proximal end 602p thereof and/or through the opening 604. The open proximal end 602p can optionally include an end cap (not shown) closing the proximal end 602p such that loose tabs in the chamber 612 cannot be released through the proximal end 602p without first releasing the end cap. The end cap and the lever can both be release mechanisms for the instrument 600.

Figure 34:
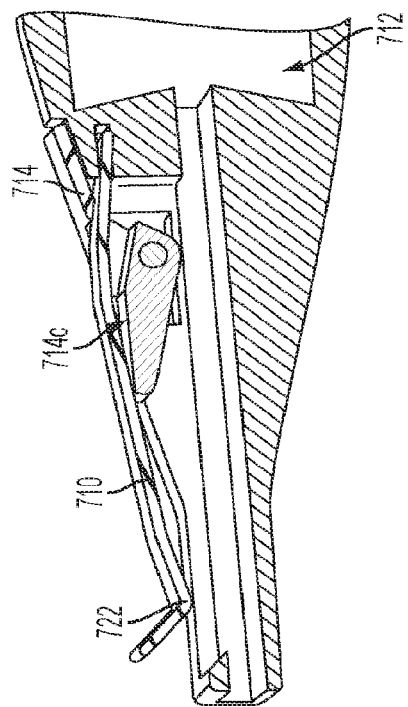
FIG. 34 is another partial cross-sectional view of the instrument of FIG. 30.

FIGS. 30-34 illustrate another embodiment of a surgical instrument 700 configured to break and retain multiple reduction tabs of one or more surgical implants. The surgical instrument 700 includes a shaft 702 having an opening 704 at a distal end thereof, a retention element 710, a chamber 712 formed in the shaft 702, and a release mechanism 714. Similar to the retention element 610 in the embodiment of FIGS. 24-29, the retention element 710 can be spring biased by having a proximal end thereof attached to the shaft 702 by compression fit as in the illustrated embodiment or in another way, with a distal end of the retention element 710 being freely movable relative to the shaft 702. The release mechanism 714 can, similar to the release mechanism 614 in the embodiment of FIGS. 24-29, include a cam 714c and a lever configured to be selectively, manually actuatable to move the retention element 710 between first and second configurations to allow broken reduction tabs to be selectively released from the shaft 702 through the opening 704 and/or to allow an unbroken reduction tab held by a pinch point 724 of the retention element 714 to be released from the instrument 700 through the opening 704. FIGS. 30-33 show the retention element 710 in the first configuration, and FIG. 34 shows the retention element 710 in the second configuration.

Similar to the chamber 412 of the embodiment illustrated in FIGS. 15-19, the chamber 712 can be configured to loosely retain broken retention tabs therein, and the shaft 702 can be configured to release broken retention tabs retained therein through an open proximal end 702p thereof and/or through the opening 704. The open proximal end 702p can optionally include an end cap (not shown) closing the proximal end 702p such that loose tabs in the chamber 712 cannot be released through the proximal end 702p without first releasing the end cap. The end cap and the lever can both be release mechanisms for the instrument 700.

Figure 35:
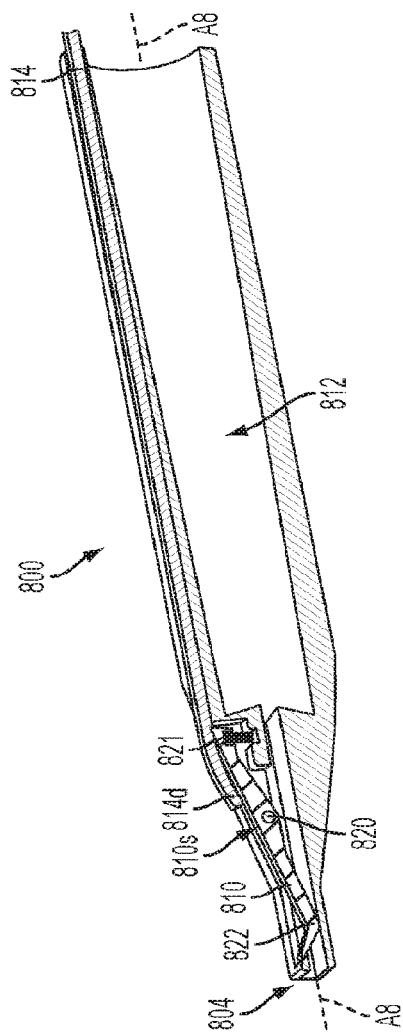
FIG. 35 is a cross-sectional view of another embodiment of a surgical instrument configured to break and retain surgical reduction tabs.

FIG. 35 illustrates another embodiment of a surgical instrument 800 configured to configured to break and retain multiple reduction tabs of one or more surgical implants. The surgical instrument 800 includes a shaft 802 having an opening 804 at a distal end thereof, a retention element 810, a chamber 812 formed in the shaft 802, and a release mechanism 814. The retention element 810 can be spring loaded by, e.g., having a proximal end thereof attached to the shaft 802, e.g., using a spring 821, and having an intermediate point thereof attached to the shaft 802 at a pivot point thereof, e.g., using a pin 820, similar to the retention element 410 of the embodiment illustrated in FIGS. 15-19. The release mechanism 814 can include a slidable bar configured to be selectively, manually actuatable to move the retention element 810 between first and second configurations to allow broken reduction tabs to be selectively released from the shaft 802 through the opening 804 and/or to allow an unbroken reduction tab held by a pinch point 822 of the retention element 810 to be released from the instrument 800 through the opening 804. The slidable bar can be configured to be longitudinally movable, e.g., parallel to a longitudinal axis A8 of the shaft 802, to pivot the retention element 810 to about the pin 820, thereby moving the punch point 822 up (e.g., radially outward) and down (e.g., radially inward). A distal end 814d of the release mechanism 814 can be configured to slide along a surface 810s of the retention element 810 as the release mechanism 814 is selectively moved back and forth to selectively pivot the retention element 810. A proximal portion of the release mechanism 814 can extend proximally beyond a proximal end 802p of the shaft 802, thereby facilitating manual sliding movement of the release mechanism 814.

Similar to the chamber 412 of the embodiment illustrated in FIGS. 15-19, the chamber 812 can be configured to loosely retain broken retention tabs therein, and the shaft 802 can be configured to release broken retention tabs retained therein through an open proximal end 802p thereof and/or through the opening 804. The open proximal end 802p can optionally include an end cap (not shown) closing the proximal end 802p such that loose tabs in the chamber 812 cannot be released through the proximal end 802p without first releasing the end cap. The end cap and the slidable bar can both be release mechanisms for the instrument 800.

Figure 36:
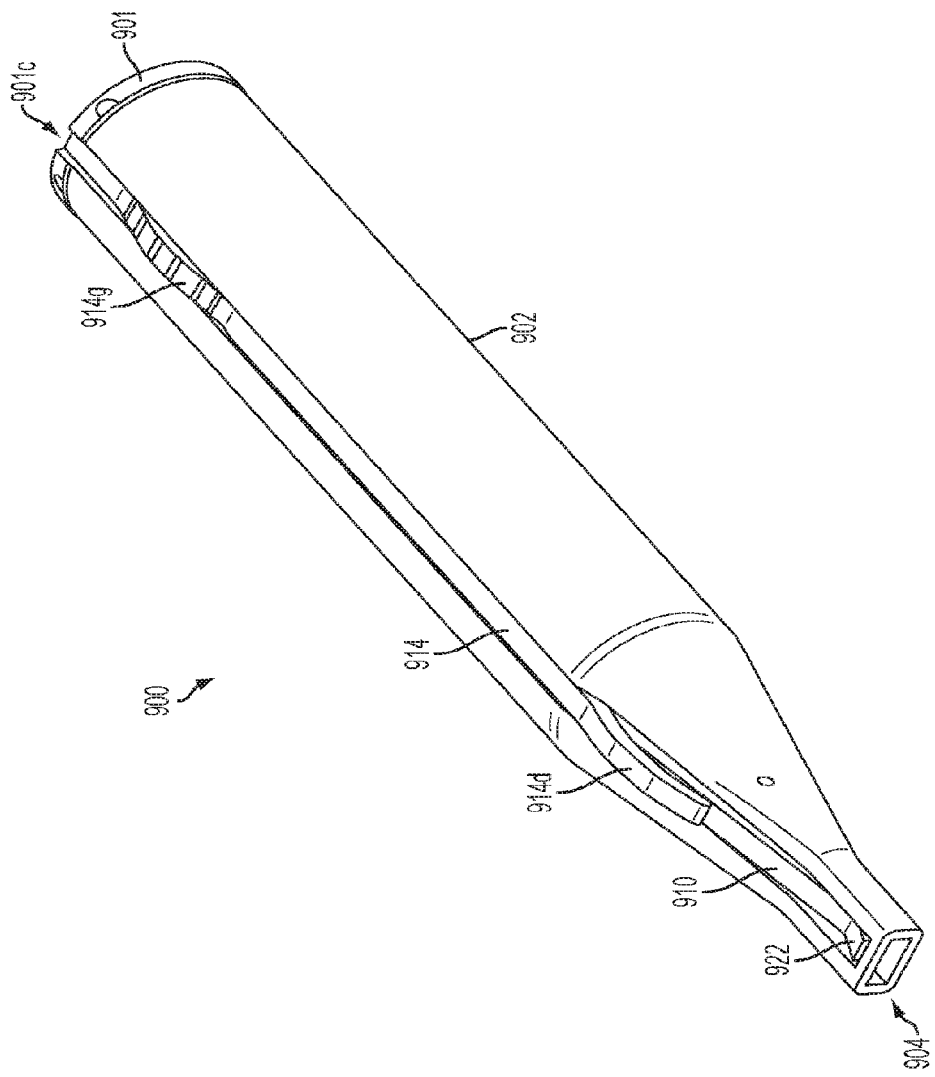
FIG. 36 is a perspective view of yet another embodiment of a surgical instrument configured to break and retain surgical reduction tabs.
Figure 37:
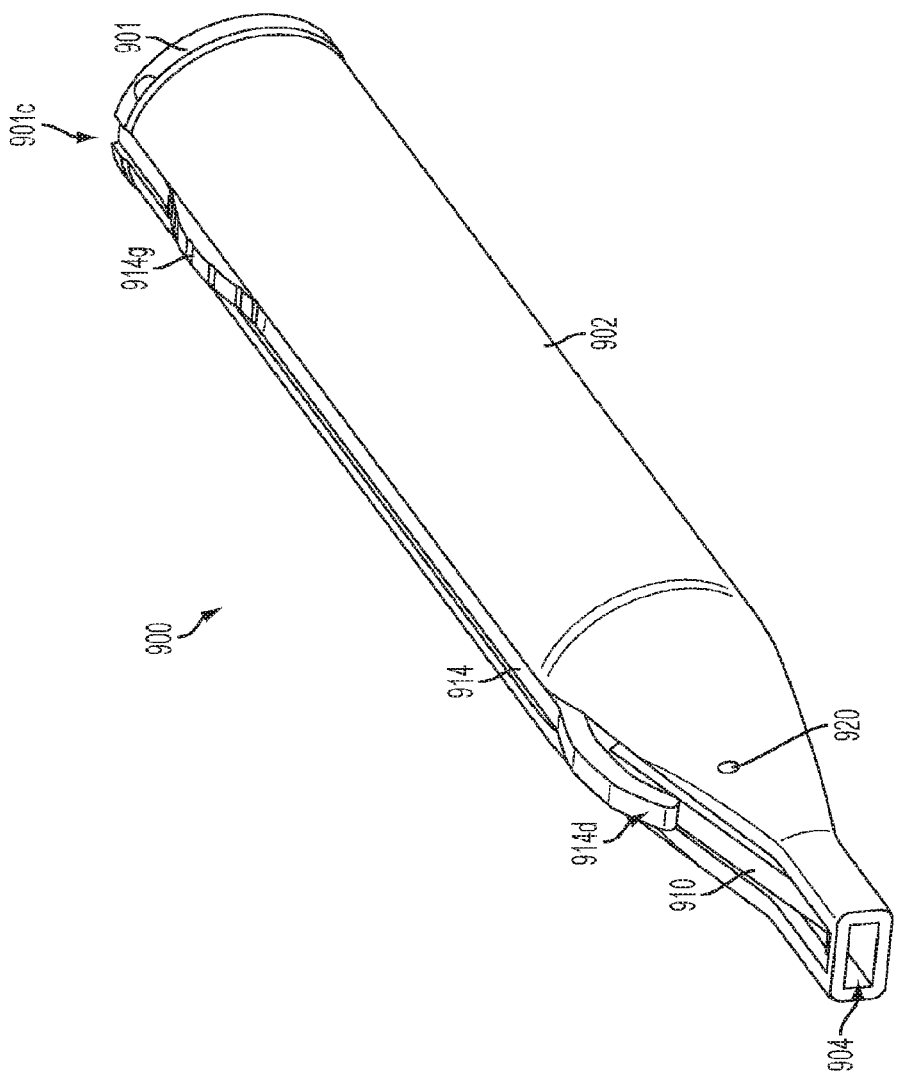
FIG. 37 is another perspective view of the instrument of FIG. 36.

FIGS. 36 and 37 illustrate another embodiment of a surgical instrument 900 configured to break and retain multiple reduction tabs of one or more surgical implants. The surgical instrument 900 includes a shaft 902 having an opening 904 at a distal end thereof, a retention element 910, a chamber (not shown) formed in the shaft 902, and a release mechanism 914. The retention element 910 can be spring loaded by, e.g., having a proximal end thereof attached to the shaft 902, e.g., using a spring, and having an intermediate point thereof attached to the shaft 902 at a pivot point thereof, e.g., using a pin 920, similar to the retention element 410 of the embodiment illustrated in FIGS. 15-19.

Similar to the release mechanism 814 of the embodiment illustrated in FIG. 35, the release mechanism 914 can include a slidable bar configured to be selectively, manually actuatable to move the retention element 910 between first and second configurations to allow broken reduction tabs to be selectively released from the shaft 902 through the opening 904 and/or to allow an unbroken reduction tab held by a pinch point 922 of the retention element 910 to be released from the instrument 900 through the opening 904. The slidable bar can be configured to be longitudinally movable, e.g., parallel to a longitudinal axis A9 of the shaft 902, to pivot the retention element 910 up and down. A distal end 914d of the release mechanism 914 can be configured to slide along a surface 910s of the retention element 910 as the release mechanism 914 is selectively moved back and forth to selectively pivot the retention element 910. A proximal portion of the release mechanism 914 can include one or more grip features 914g configured to facilitate hand gripping of the release mechanism 914. The one or more grip features 914g in this illustrated embodiment includes a ridged, raised protrusion, but as mentioned above, grip features of an instrument can be configured in a variety of ways.

Similar to the chamber 412 of the embodiment illustrated in FIGS. 15-19, the chamber can be configured to loosely retain broken retention tabs therein, and the shaft 902 can be configured to release broken retention tabs retained therein through a proximal end 902p thereof and/or through the opening 904. The proximal end 902p can optionally include an end cap 901 closing the proximal end 902p such that loose tabs in the chamber cannot be released through the proximal end 902p without first releasing the end cap 901. The end cap 901 in the illustrated embodiment is threadably connected to the proximal end 902p of the shaft 902, but as mentioned above, the end cap 901 can be attached to the shaft 902 in any of a variety of ways. The end cap 901 and the slidable bar can both be release mechanisms for the instrument 900. The end cap 901 can have a cut-out 901c therein configured to allow slidable movement of the slidable bar therein.

Figure 38:
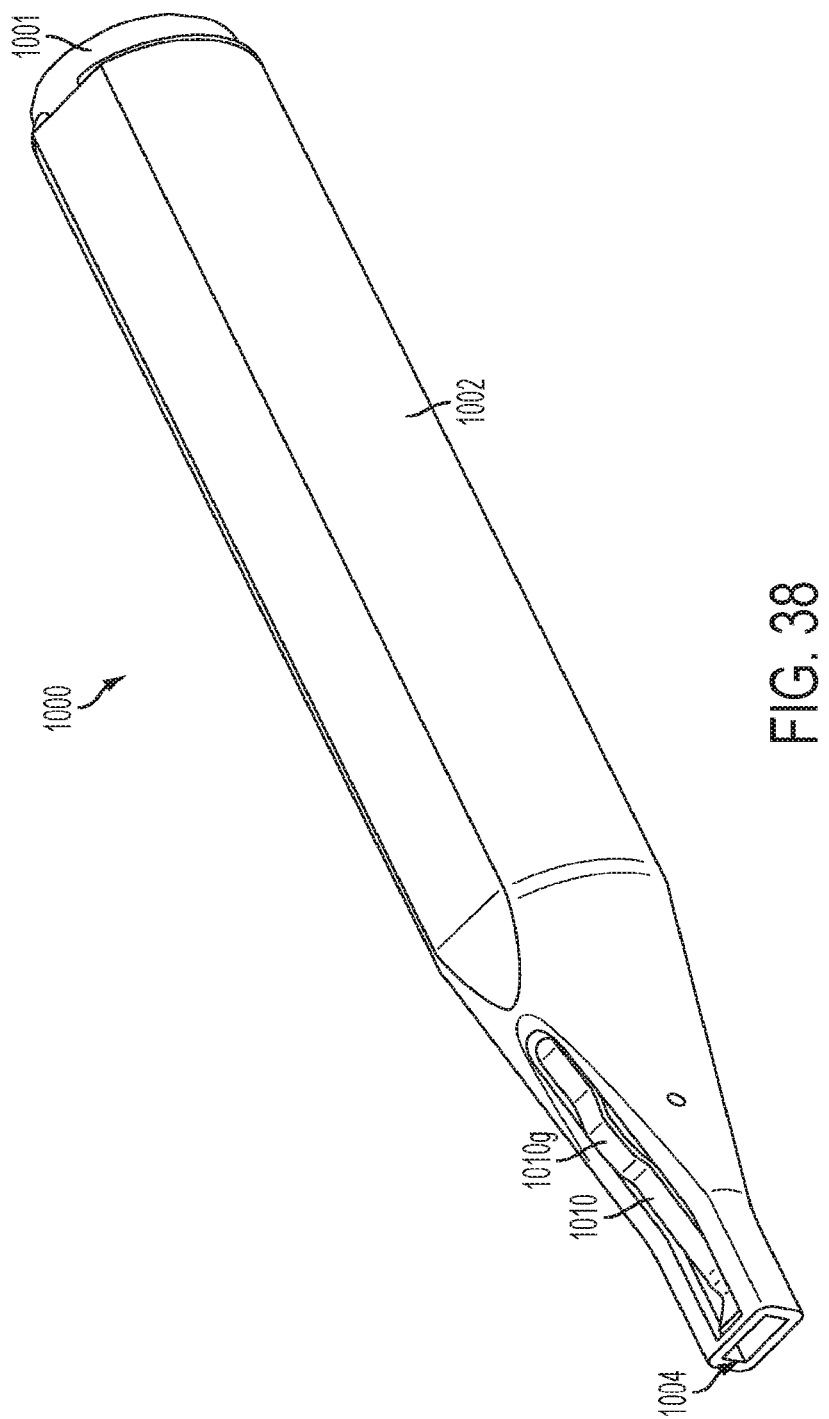
FIG. 38 is a perspective view of another embodiment of a surgical instrument configured to break and retain surgical reduction tabs.
Figure 39:
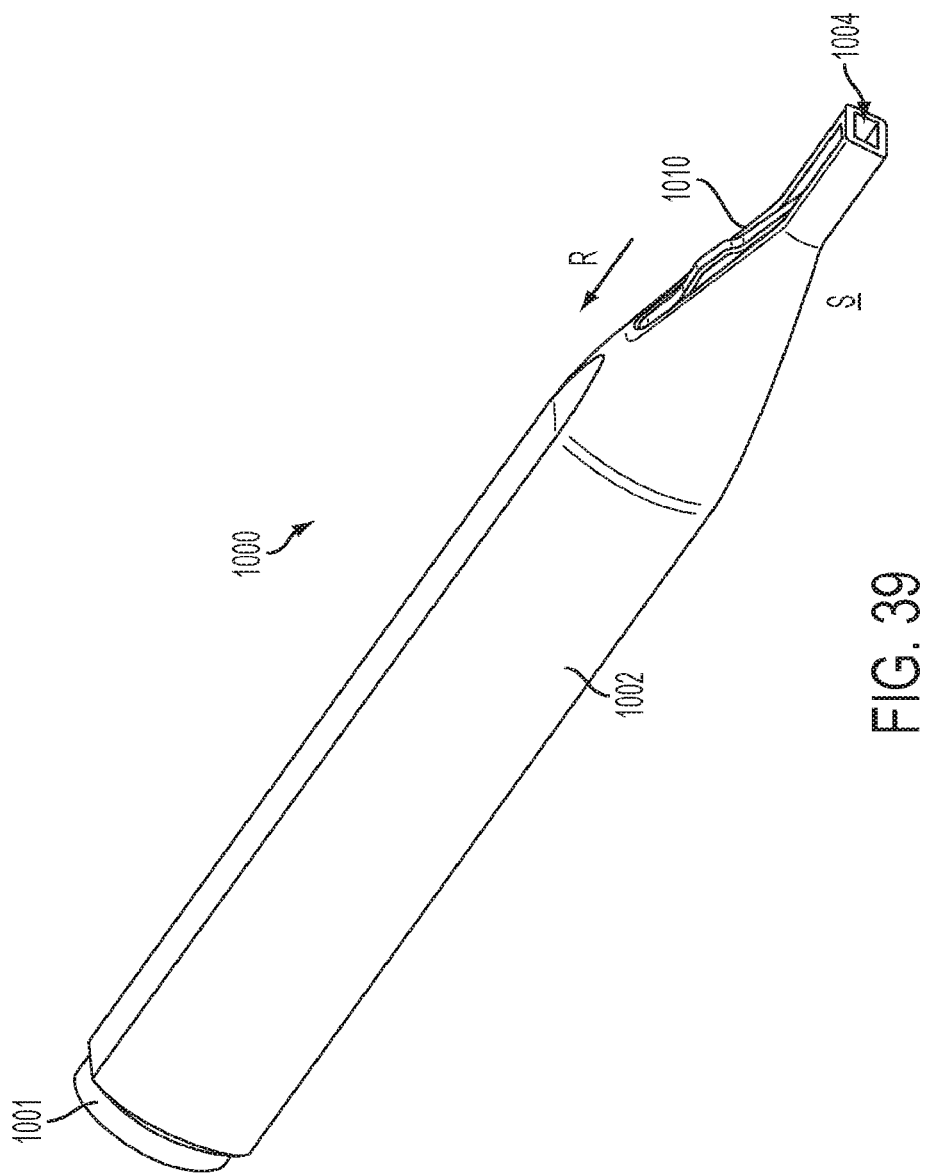
FIG. 39 is another perspective view of the instrument of FIG. 38.
Figure 40:
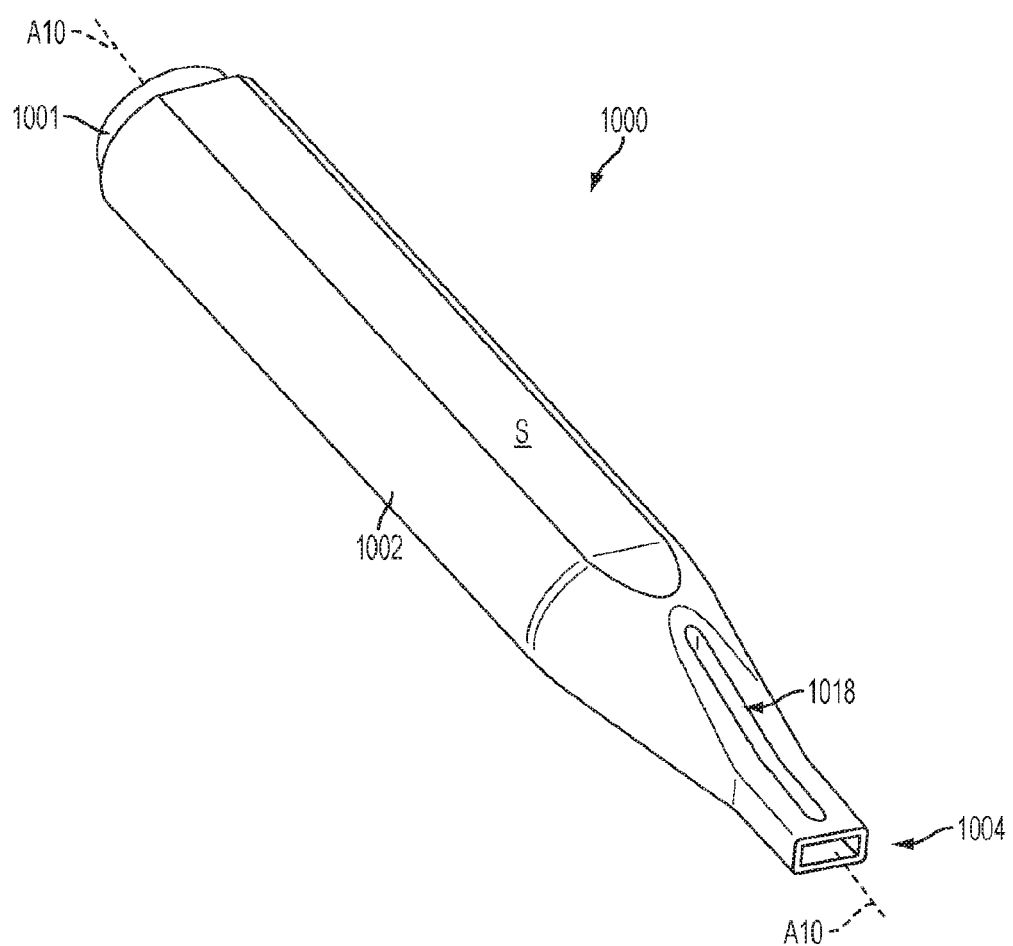
FIG. 40 is yet another perspective view of the instrument of FIG. 38.

FIGS. 38-40 illustrate another embodiment of a surgical instrument 1000 configured to break and retain multiple reduction tabs of one or more surgical implants. The surgical instrument 1000 includes a shaft 1002 having an opening 1004 at a distal end thereof, a retention element 1010, and a chamber (not shown) formed in the shaft 1002. Similar to the retention element 510 of the embodiment illustrated in FIGS. 20-23, the retention element 1010 can be configured as a release mechanism of the instrument 1000 by being configured to be selectively, manually movable between a first configuration in which the retention element 1010 can be configured to hold a reduction tab inserted into the opening 1004 in a fixed position, and a second configuration in which the retention element 1010 can be configured to allow a reduction tab inserted into the opening 1004, as well as any reduction tabs disposed within the chamber to be released from the shaft 1002 through the opening 1004.

The retention element 1010 can be configured to be selectively, manually movable in a variety of ways, such as by manually moving the retention element 1010 away from a side S of the shaft 1002 to which the retention element 1010 is biased, e.g., in an angled proximal direction indicated by arrow R in FIG. 39, to move the retention element 1010 from the first configuration to the second configuration. The retention element 1010 can be moved in a direction opposite to the arrow R to move the retention element 1010 from the second configuration to the first configuration. The retention element 1010 can be biased to the first configuration such that removing manual force from the retention element 1010 when the retention element 1010 is in the second configuration can cause the retention element 1010 to automatically move to from the second configuration to the first configuration. The direction of the arrow R is a non-limiting direction. The retention element 1010 can include one or more grip features 1010g configured to facilitate hand gripping of the retention element 1010. The one or more grip features 1010g in this illustrated embodiment includes a raised protrusion, but as mentioned above, grip features of an instrument can be configured in a variety of ways.

Similar to the slot 118 in the embodiment illustrated in FIGS. 1-7, the shaft 1002 can include a slot 1018, shown in FIG. 40, formed therein that is configured to facilitate release of broken tabs from within the shaft 1002. The slot 1018 can be a longitudinal slot extending parallel to a longitudinal axis A10 of the shaft 1002 and can be on a same side S of the shaft 1002 to which the retention element 1010 can be biased, and can be opposite a pinch point (not shown) of the retention element 1010, which can help facilitate removal of one or more reduction tabs in a distal portion of the device.

Similar to the chamber 412 of the embodiment illustrated in FIGS. 15-19, the chamber can be configured to loosely retain broken retention tabs therein, and the shaft 1002 can be configured to release broken retention tabs retained therein through a proximal end 1002p thereof and/or through the opening 1004. Similar to the embodiment illustrated in FIGS. 36 and 37 that includes the end cap 901, the proximal end 1002p of the shaft 1002 can include an end cap 1001.

FIGS. 41 and 42 illustrate another embodiment of a surgical instrument 1100 configured to break and retain multiple reduction tabs of one or more surgical implants. The surgical instrument 1100 includes a shaft 1102 having an opening 1104 at a distal end thereof, a retention element 1110, a chamber (not shown) formed in the shaft 1102, and an end cap 1101. Similar to the retention element 1010 of the embodiment illustrated in FIGS. 38-40, the retention element 1110 can be configured as a release mechanism of the instrument 1100 by being configured to be selectively, manually movable between a first configuration in which the retention element 1110 can be configured to hold a reduction tab inserted into the opening 1104 in a fixed position, and a second configuration in which the retention element 1110 can be configured to allow a reduction tab inserted into the opening 1104, as well as any reduction tabs disposed within the chamber to be released from the shaft 1102 through the opening 1104. The retention element 1110 can be configured to be selectively, manually movable in a variety of ways, such as by manually moving the retention element 1110 away from a side S11 of the shaft 1102 to which the retention element 1110 is biased. Also, the retention element 1110 can include one or more grip features 1110g, e.g., a raised protrusion, configured to facilitate hand gripping of the retention element 1110. The end cap 1101 and the retention element 1110 can both be release mechanisms for the instrument 1100.

Figure 43:
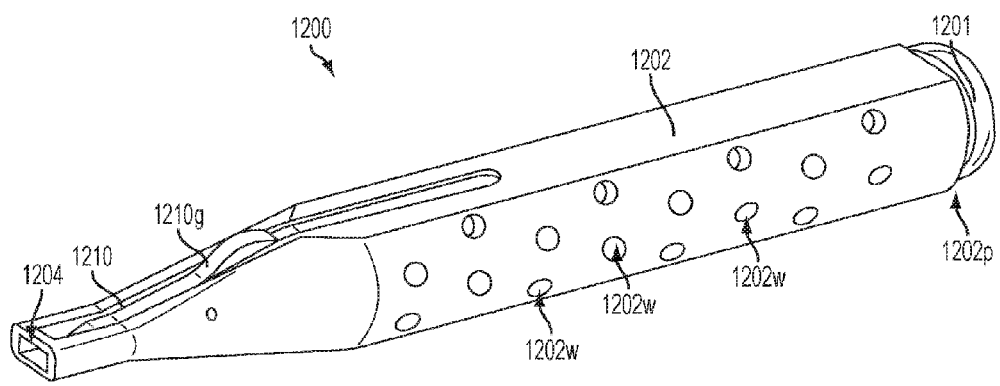
FIG. 43 is a perspective view of another embodiment of a surgical instrument configured to break and retain surgical reduction tabs.
Figure 44:
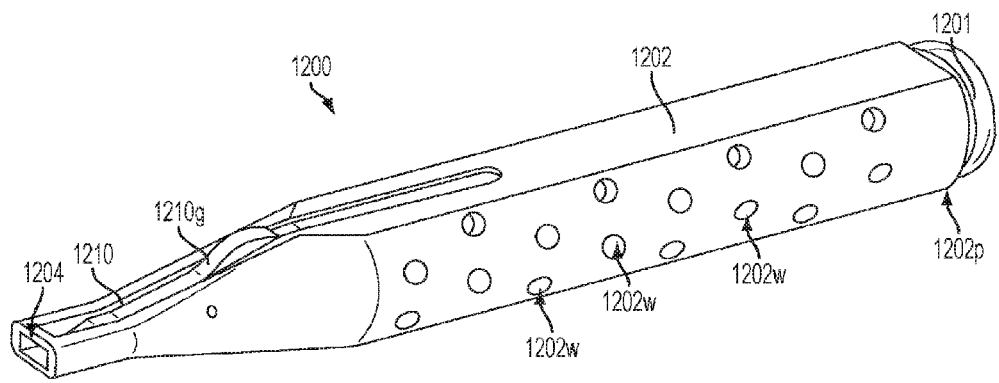
FIG. 44 is another perspective view of the instrument of FIG. 43.
Figure 45:
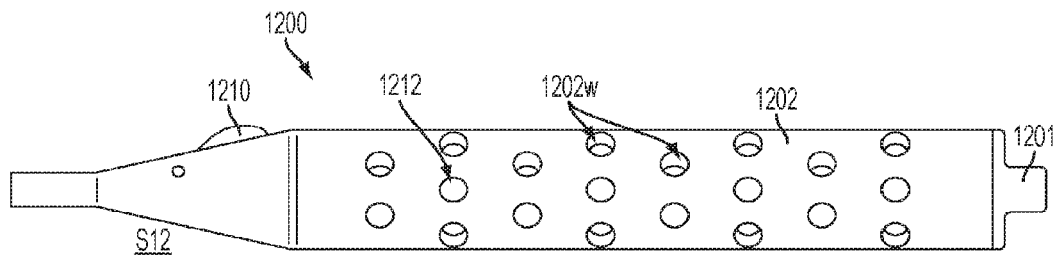
FIG. 45 is still another perspective view of the instrument of FIG. 43.

FIGS. 43-45 illustrate another embodiment of a surgical instrument 1200 configured to break and retain multiple reduction tabs of one or more surgical implants. The surgical instrument 1200 includes a shaft 1202 having an opening 1204 at a distal end thereof, a retention element 1210, a chamber 1212 formed in the shaft 1202, and an end cap 1201. The shaft 1202 can have one or more windows 1202w formed therein. In the illustrated embodiment, the shaft 1202 includes a plurality of windows formed therein in a proximal portion thereof adjacent the chamber 1212. The windows 1202w can be configured to allow visualization of the chamber 1212, which can facilitate determining whether the chamber 1212 is becoming so full of broken reduction tabs such that broken reduction tabs should be released therefrom, e.g., through the opening 1204 and/or through the shaft's proximal end 1202p (with the end cap 1202 actuated out of the way). The one or more windows 1202w can have a variety of sizes, shapes, and configurations. The one or more windows 1202w are each circular cut-outs in the shaft 1202 each having a same size in the illustrated embodiment, but any one of more of the windows 1202w can have a shape different from any one or more of the other windows 1202w, and a size different from any one or more of the other windows 1202w. Although the one or more windows 1202w are cut-outs in the illustrated embodiment, the one or more windows 1202w can be transparent portions of the shaft 1202w instead of cut-outs therein, which can help contain any fluid and/or other debris that enters the chamber 1212 through the opening 1204 from passing out of the chamber 1212 through any of the windows 1202w.

Similar to the retention element 1010 of the embodiment illustrated in FIGS. 38-40, the retention element 1210 can be configured as a release mechanism of the instrument 1200 by being configured to be selectively, manually movable between a first configuration in which the retention element 1210 can be configured to hold a reduction tab inserted into the opening 1204 in a fixed position, and a second configuration in which the retention element 1210 can be configured to allow a reduction tab inserted into the opening 1204, as well as any reduction tabs disposed within the chamber to be released from the shaft 1202 through the opening 1204. The retention element 1210 can be configured to be selectively, manually movable in a variety of ways, such as by manually moving the retention element 1210 away from a side S12 of the shaft 1202 to which the retention element 1210 is biased. Also, the retention element 1210 can include one or more grip features 1210g, e.g., a raised protrusion, configured to facilitate hand gripping of the retention element 1210. The end cap 1201 and the retention element 1210 can both be release mechanisms for the instrument 1200.

Figure 46:
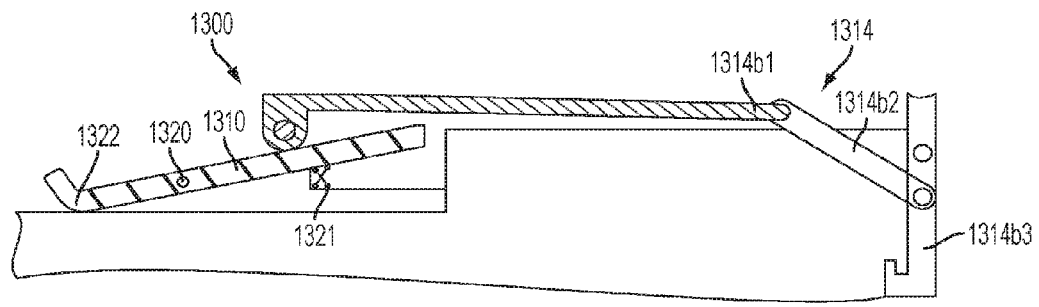
FIG. 46 is a partial cross-sectional view of another embodiment of a surgical instrument configured to break and retain surgical reduction tabs.

FIG. 46 illustrates another embodiment of a surgical instrument 1300 configured to break and retain multiple reduction tabs of one or more surgical implants. The surgical instrument 1300 includes a shaft (not shown) having an opening (not shown) at a distal end thereof, a retention element 1310, a chamber (not shown) formed in the shaft, and a release mechanism 1314. The retention element 1310 can be spring loaded by, e.g., having a proximal end thereof attached to the shaft using a spring element 1321, e.g., a coil spring, a volute spring, a bellows, an elastic band, etc., such that the retention element 1310 can pivot about a pivot pin 1320. The release mechanism 1314 can, similar to the release mechanism 814 in the embodiment shown in FIG. 35, include a slidable bar configured to be selectively, manually actuatable to move the retention element 1310 between first and second configurations to allow broken reduction tabs to be selectively released from the shaft through the opening and/or to allow an unbroken reduction tab held by a pinch point 1322 of the retention element 1310 to be released from the instrument 1300 through the opening. The slidable bar can include first, second, and third bars 1314b1, 1314b2, 1314b3 pivotally connected to one another at first and second pivot points 1314a, 1314b such that moving the third bar 1314b3, e.g., by manually moving the third bar 1314b3 up and down, can slide the release mechanism 1314, e.g., a distal end of the first bar 1314a, along the retention element 1310.

Figure 47:
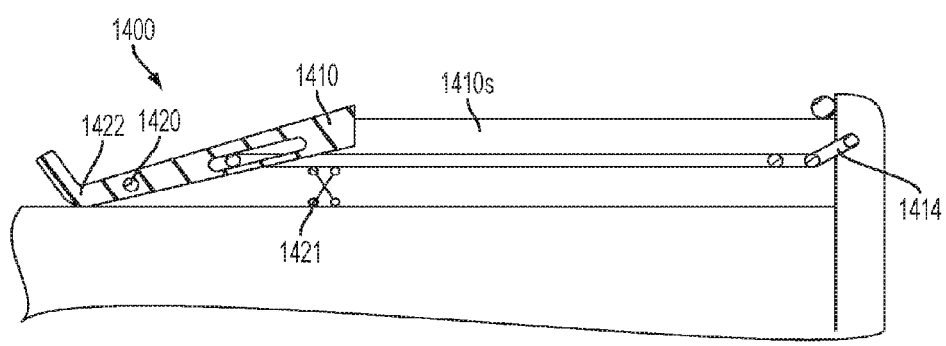
FIG. 47 is a partial cross-sectional view of yet another embodiment of a surgical instrument configured to break and retain surgical reduction tabs.
Figure 48:
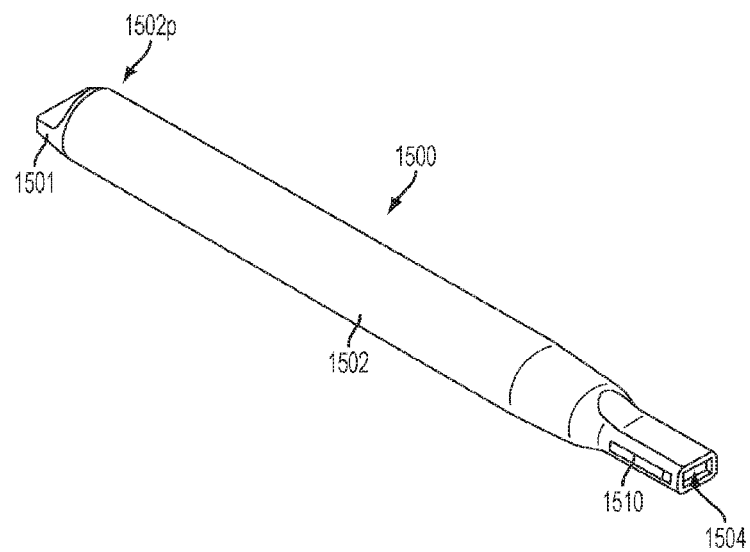
FIG. 48 is a perspective view of another embodiment of a surgical instrument configured to break and retain surgical reduction tabs.
Figure 49:
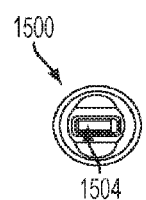
FIG. 49 is a distal end view of the instrument of FIG. 48.
Figure 50:
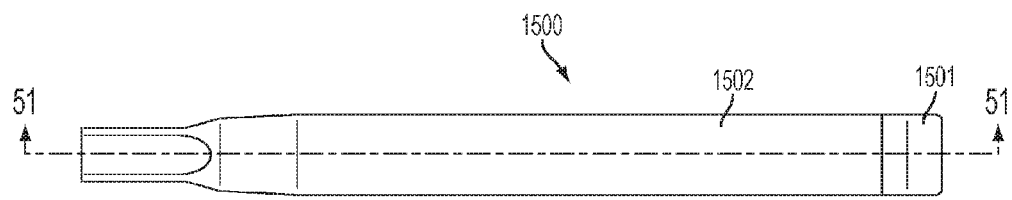
FIG. 50 is a side view of the instrument of FIG. 48.

FIG. 47 illustrates another embodiment of a surgical instrument 1400 configured to break and retain multiple reduction tabs of one or more surgical implants. The surgical instrument 1400 includes a shaft (not shown) having an opening (not shown) at a distal end thereof, a retention element 1410, a chamber (not shown) formed in the shaft, and a release mechanism 1414. The retention element 1410 can be spring loaded by, e.g., having a proximal end thereof attached to the shaft using a spring element 1421, e.g., a coil spring, a volute spring, a bellows, an elastic band, etc., such that the retention element 1410 can pivot about a pivot pin 1420. The release mechanism 1414 can, similar to the release mechanism 814 in the embodiment shown in FIG. 35, include a slidable bar configured to be selectively, manually actuatable to move the retention element 1410 between first and second configurations to allow broken reduction tabs to be selectively released from the shaft through the opening and/or to allow an unbroken reduction tab held by a pinch point 1422 of the retention element 1410 to be released from the instrument 1400 through the opening. The release mechanism 1414 can be slidably coupled to the release mechanism 1414 such that the release mechanism 1414, e.g., a distal end thereof, can be slidably received in a slot 1410s formed in the retention element 1410.

FIGS. 48-54 illustrate another embodiment of a surgical instrument 1500 configured to break and retain multiple reduction tabs of one or more surgical implants. The surgical instrument 1500 includes a shaft 1502 having an opening 1504 at a distal end thereof, a retention element 1510, a chamber 1512 formed in the shaft 1502, and an end cap 1501.

Figure 54:
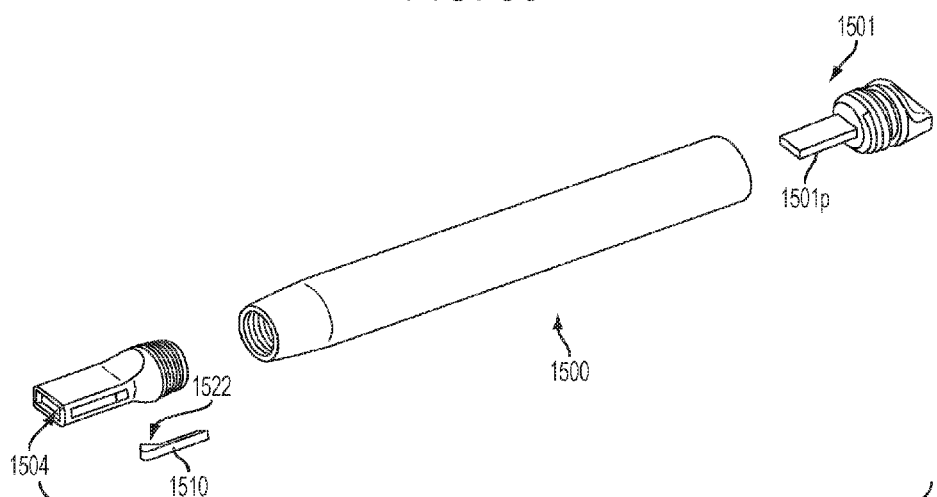
FIG. 54 is an exploded view of the instrument of FIG. 48.

FIG. 54 shows a distal portion of the instrument 1500 that includes the opening 1504 and the retention element 1510 as having a threaded proximal portion configured to threadably engage a threaded distal portion of the shaft 1502. This distal portion can be attached to the shaft 1502 in another way, e.g., welding, snap fit, etc. In an exemplary embodiment, this distal portion of the instrument 1500 is not removable from the shaft 1502 once attached thereto but is threaded with the shaft 1502 so as to facilitate manufacturing of the instrument 1500. Alternatively, this distal portion of the instrument 1500 can be configured to be removable from the shaft 1502 by unthreading the distal portion of the instrument 1500 from the shaft 1502, which can facilitate cleaning and/or sterilization of the instrument 1500.

Similar to that discussed above regarding the embodiment illustrated in FIGS. 15-19, the retention element 1510 can be spring loaded, e.g., having a proximal end thereof attached to the shaft 1502, e.g., by being welded thereto as a cantilevered spring. FIGS. 48-53 show the instrument 1500 with the retention element 1510 in a first configuration in which the retention element 1510 can be configured to hold a reduction tab inserted into the opening 1504 in a fixed position and held therein by a pinch point 1522 of the retention element 1510. The retention element 1510 can be configured to move between the first configuration and a second configuration (not shown) in which the retention element 1510, e.g., a portion thereof including the pinch point 1522, has moved radially outward relative to the shaft 1502, to holds reduction tab. The first configuration of the retention element 1510 can be the neutral or default configuration of the retention element 1510, as in the illustrated embodiment, such that the retention element 1510 is biased to a position in which the pinch point 1522 is biased radially inward relative to the shaft 1502, which can facilitate secure holding of a tab by the pinch point 1522.

The retention element 1510 can be positioned on a side of the opening 1504, e.g., along a short side of the opening 1504, configured to be adjacent to a side edge of a reduction tab inserted into the opening 1504. In this way, the retention element 1510 can be configured to interchangeably hold reduction tabs having a concave side or a convex side facing to a same side of the opening 1504, e.g., to a long side of the opening 1504. In other words, the retention element 1510 can be configured to hold a reduction tab having a curved shape regardless of the tab's orientation relative to the opening 1504 when inserted into the opening 1504.

The instrument 1500 includes only one retention element 1510, but the instrument 1500 can include a plurality of retention elements each configured to simultaneously hold a same tab within the opening 1504. Having a plurality of retention elements can help securely hold a tab in a fixed position within the opening 1504, can facilitate the holding of differently sized reduction tabs that are inserted into the opening 1504, and/or can allow each of the retention elements to deflect less when engaging a tab so as to help the instrument 1500 take up less space within a surgical area. For example, the instrument 1500 can include a second retention element (not shown) on an opposite side of the opening 1504 from the retention element 1510.

Similar to that discussed above regarding the embodiment illustrated in FIGS. 15-19, the end cap 1501 can be a release mechanism for the instrument 1500. Also similar to the embodiment illustrated in FIGS. 15-19, the chamber 1512 can be configured to loosely retain broken retention tabs therein, and the shaft 1502 can be configured to release broken retention tabs retained therein through a proximal end 1502*p* thereof. Similar to the embodiment illustrated in FIGS. 36 and 37 that includes the end cap 901, the proximal end 1502*p* of the shaft 1502 can include the end cap 1501. The end cap 1501 is removably and replaceably coupled to the shaft 1502 via a threaded connection in the illustrated embodiment, but as mentioned above, the end cap 1501 can be removably and replaceably attached to the shaft 1502 in other ways, e.g., a magnetic attachment, a snap fit, etc.

The end cap 1501 can include a protrusion 1501*p* configured to be inserted into the opening 1504 when the end cap 1501 is not attached to the shaft's proximal end 1502*p*. The protrusion 1501*p* can be configured to engage and push proximally at least one broken tab within the instrument 1500 when the protrusion 1501*p* is inserted into the opening 1504. The protrusion 1501*p* can thus help broken tab(s) be quickly removed from within the shaft 1502 even if the tab is being held by the pinch point 1522, help unjam any broken tab(s) within the shaft 1502 in the unlikely event that the tab(s) become jammed therein, and/or help clear foreign material (e.g., tissue, blood, etc.) other than broken tab(s) from within the shaft 1502. The protrusion 1501*p* can be inserted into the opening 1504 whether or not any broken tabs are within the chamber 1512 and/or are being held by the retention element 1510, which can facilitate clearing foreign material to, e.g., clear space for broken tabs to be disposed within the instrument 1500. Since the retention element 1510 can be biased to the first configuration, as mentioned above, inserting the protrusion 1501*p* into the opening 1504 can allow a tab being held by the pinch point 1522 to be pushed proximally into the chamber 1512 so as to allow the tab to be removed from the instrument 1500, e.g., by exiting through the shaft's proximal end 1502*p* when the cap 1501 is not attached thereto.

The protrusion 1501*p* can have a variety of sizes, shapes, and configurations. The protrusion 1501*p* can have a size and shape corresponding to a size and shape of the opening 1504 so as to help maximize an amount of space the protrusion 1501*p* can clear within the instrument 1500 when inserted into the opening 1504. In the illustrated embodiment, the protrusion 1501*p* has a rectangular box shape and a rectangular cross-sectional shape, which corresponds to a rectangular shape and a rectangular cross-sectional shape of the opening 1504.

Figure 53:
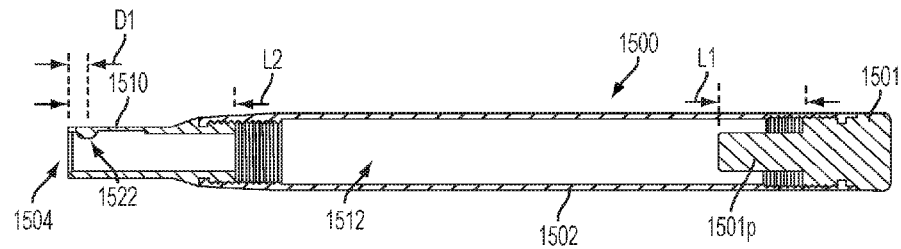
FIG. 53 is a cross-sectional view of the instrument of FIG. 52.

As shown in FIG. 53, the protrusion 1501*p* can have a longitudinal length L1 that is equal to or greater than a distance D1 between a distal end of the opening 1504 and the pinch point 1522 of the retention element 1510. The protrusion 1501*p* being at least as long as this distance D1 can help ensure that the protrusion 1501*p* is able to push proximally a broken tab (not shown) being held at the pinch point 1522 by the retention element 1510. In an exemplary embodiment, the protrusion's longitudinal length L1 can be equal to or greater than a longitudinal length L2 of the opening 1504, which can help ensure that the protrusion 1501*p* is able to move proximally through an entire length of the opening 1504 and thereby help clear any foreign material from the opening 1504.

Figure 51:
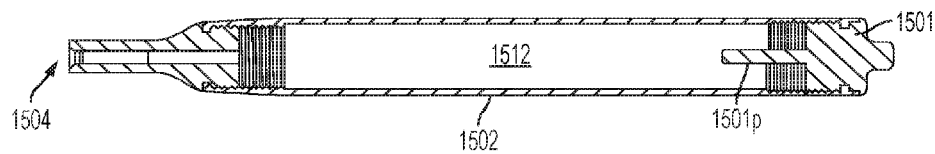
FIG. 51 is a cross-sectional view of the instrument of FIG. 50.
Figure 52:
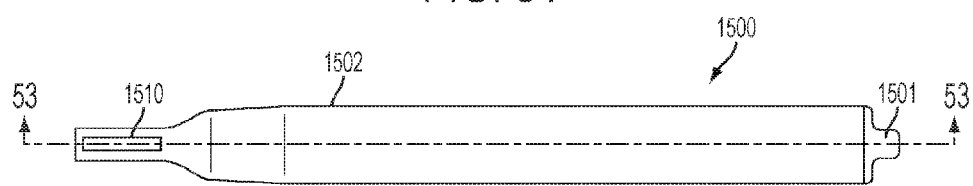
FIG. 52 is another side view of the instrument of FIG. 48.
Figure 58:
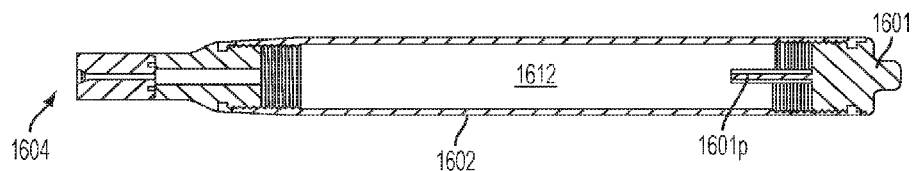
FIG. 58 is a cross-sectional view of the instrument of FIG. 57.
Figure 59:
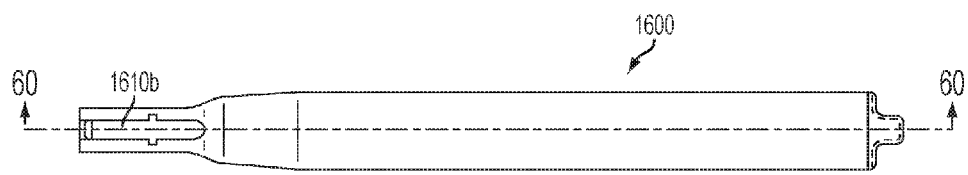
FIG. 59 is another side view of the instrument of FIG. 55.
Figure 60:
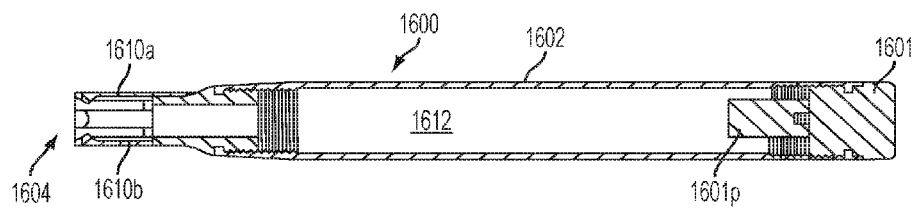
FIG. 60 is a cross-sectional view of the instrument of FIG. 59.
Figure 61:
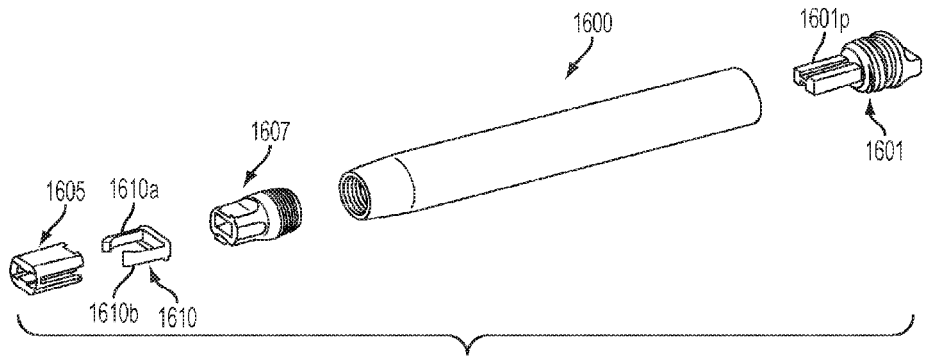
FIG. 61 is an exploded view of the instrument of FIG. 55.

The protrusion 1501*p* can extend distally from the end cap 1501, as shown in FIGS. 58, 60, and 61. The protrusion 1501*p* can be configured to be at least partially disposed within the chamber 1512 when the end cap 1501 is attached to the shaft 1502, as shown in FIGS. 51 and 53, in which the protrusion 1501*p* is shown partially disposed in a proximal portion of the chamber 1512. The protrusion 1501*p* can thus be unobtrusively coupled to the instrument 1500 so as to not interfere with a user's handling of the instrument 1500.

FIGS. 55-61 illustrate another embodiment of a surgical instrument 1600 configured to break and retain multiple reduction tabs of one or more surgical implants. The surgical instrument 1600 includes a shaft 1602 having an opening 1604 at a distal end thereof, a retention element 1610, a chamber 1612 formed in the shaft 1602, and an end cap 1601 having a protrusion 1601*p* extending therefrom.

The end cap 1601 can be configured similar to the end cap 1501 of the embodiment illustrated in FIGS. 48-54. The protrusion 1601*p* can be configured similar to the protrusion 1501*p* of the embodiment illustrated in FIGS. 48-54, e.g., be configured to be insertable into the opening 1604, be configured to be at least partially disposed in the chamber 1612 when the cap 1601 is attached to the shaft 1602, etc.

FIG. 61 shows a distal portion of the instrument 1600 that includes the opening 1604 that extends through a proximal tip component 1605, a distal tip component 1607, and the retention element 1610 as having a threaded proximal portion, e.g., on the proximal tip component 1605, configured to threadably engage a threaded distal portion of the shaft 1602. The distal portion of the instrument 1600 can be attached to the shaft 1602 in another way, e.g., welding, snap fit, etc. Similar to that discussed above with respect to the distal portion of the instrument 1500 of the embodiment illustrated in FIGS. 48-54, this distal portion of the instrument 1600 is not removable from the shaft 1602 once attached thereto, but this distal portion of the instrument 1600 can be removable from the shaft 1602.

As also shown in FIG. 61, the retention element 1610 can include a plurality of retention elements, e.g., first and second opposed retention elements 1610*a*, 1610*b*. Similar to that discussed above regarding the embodiment illustrated in FIGS. 15-19, the retention elements 1610*a*, 1610*b* can be spring loaded. The first and second opposed retention elements 1610a, 1610b can be configured to be disposed on opposed sides of the opening 1604, e.g., along opposed short sides of the opening 1604, configured to be adjacent to opposed side edges of a reduction tab inserted into the opening 1604. In this way, the retention element 1610 can be configured to interchangeably hold reduction tabs having a concave side or a convex side facing to a same side of the opening 1604, e.g., to a long side of the opening 1604. In other words, the retention element 1610 can be configured to hold a reduction tab having a curved shape regardless of the tab's orientation relative to the opening 1504 when inserted into the opening 1504.

The first and second opposed retention elements 1610a, 1610b can be integrally formed, as in the illustrated embodiment, so as to be a single retention element component. Being a single retention element component can facilitate manufacture of the instrument 1600 by allowing for better control of manufacturing tolerances for each of the instrument's retention elements 1610a, 1610b, which can facilitate control of a distance between the retention elements 1610a, 1610b when coupled to the shaft 1604. Alternatively, the first and second opposed retention elements 1610a, 1610b can be separate components, e.g., each be configured similar to the retention element 1500 of the embodiment illustrated in FIGS. 48-54.

Each of the first and second retention elements 1610a, 1610b can be configured to move between first and second configurations, similar to that discussed above with respect to the retention element 1510 of the embodiment illustrated in FIGS. 48-54.

Figure 55:
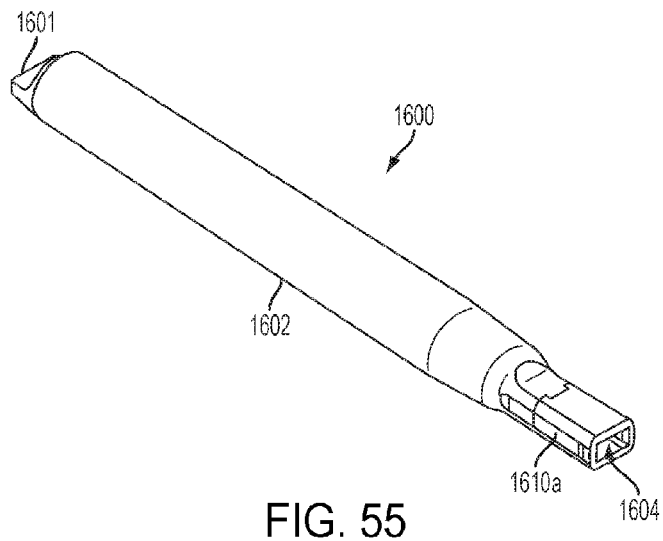
FIG. 55 is a perspective view of another embodiment of a surgical instrument configured to break and retain surgical reduction tabs.
Figure 56:
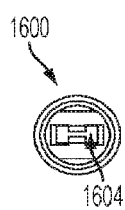
FIG. 56 is a distal end view of the instrument of FIG. 55.
Figure 57:
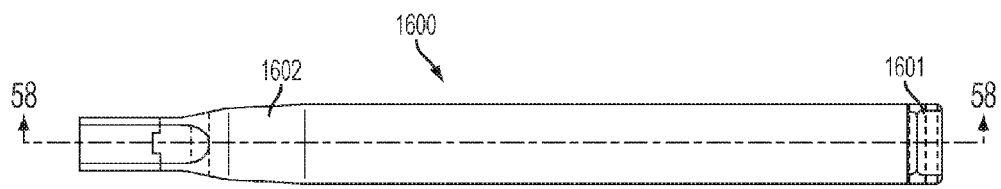
FIG. 57 is a side view of the instrument of FIG. 55.

At least a portion of the opening 1604 can have an "I" cross-sectional shape, as shown in FIGS. 55, 56, and 61. "The "I" cross-sectional shape can allow the opening 1604 to interchangeably receive reduction tabs therein having a concave side facing either long side of the opening 1604, similar to that discussed above with respect to the rectangular cross-shaped opening 104 of FIGS. 1-7. A reduced diameter portion in a middle of the "I" shape can facilitate predictable positioning of tabs sequentially inserted into the opening 1604. The "I" cross-sectional shape can help a reduction tab inserted into the opening 1604 be aligned with an immediately previous one of the tabs inserted into the opening 1604, even if the concave sides of the tabs face different directions, so as to effectively proximally push the immediately previous one of the tabs toward the chamber 1612. In other words, a mid-portion of each one of the tabs inserted into the opening 1604 can be positioned in the reduced diameter portion in a middle of the "I" shape such that at least the mid-portions of sequentially inserted tabs can be more likely to be aligned so as to allow the mid-portions to abut and facilitate pushing of a previously inserted tab.

In an exemplary embodiment, at least a distal portion of the opening 1604 can have the "I" cross-sectional shape. In this way, a reduction tab can be inserted into the opening 1604 in the predictable position facilitated by the "I" cross-sectional shape. In the illustrated embodiment, a distal portion of the opening 1604, e.g., a portion of the opening 1604 in the distal tip component 1605, has an "I" cross-sectional shape. A remainder of the opening 1604 can have another cross-sectional shape. In the illustrated embodiment, as shown in FIG. 61, a proximal portion of the opening 1604 that extends through the retention element 1610 and the proximal tip component 1607 has a rectangular cross-sectional shape.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the blades, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. A surgical apparatus, comprising:
   an elongate shaft having a proximal end and a distal end, the distal end having an opening shaped to receive a reduction tab of a U-shaped head of a surgical implant therein, the distal end being configured to be advanced into a body of a patient, the proximal end having a chamber that extends through at least a portion thereof, the chamber being in communication with the opening and configured to receive a broken-off reduction tab therein;
   a retention arm positioned at least partially within the shaft, the retention arm being configured to directly contact a reduction tab inserted into the opening to direct a force onto the reduction tab that maintains the reduction tab in a fixed position relative to the opening while the reduction tab is broken off from the surgical implant; and
   a release mechanism movable between a locked configuration and an unlocked configuration to allow release of retained broken tabs from within the chamber through the opening.

2. The apparatus of claim 1, wherein the retention arm contacts the reduction tab at a pinch point located on a portion of the retention arm.

3. The apparatus of claim 1, wherein the retention arm moves radially outward relative to the shaft as a reduction tab is inserted into the opening.

4. The apparatus of claim 1, wherein the release mechanism directly contacts at least a portion of the retention arm.

5. The apparatus of claim 1, wherein the release mechanism is spring loaded and a spring biases the release mechanism towards the locked configuration.

6. The apparatus of claim 1, wherein the release mechanism is a lever located in a recessed portion of the shaft that allows movement of the lever therein.

7. The apparatus of claim 6, wherein a distal end of the release mechanism includes a rotatable cam switch that moves the retention arm.

8. The apparatus of claim 1, wherein the release mechanism is a longitudinally slidable bar that moves the retention arm.

9. The apparatus of claim 8, wherein the slidable bar slides along a surface of the retention arm as the release mechanism moves between the locked configuration and the unlocked configuration.

10. The apparatus of claim 1, wherein the apparatus includes a plurality of retention arms configured to hold a single reduction tab disposed within the opening simultaneously.

11. The apparatus of claim 1, further comprising a jam release bar that is attached to the release mechanism, the jam release bar being movable in tandem with the release mechanism such that a portion of the jam release bar contacts a broken reduction tab disposed in the chamber and pushes the broken reduction tab out of the chamber when the release mechanism is actuated.

12. A surgical method, comprising:
disposing a first reduction tab of a U-shaped head of a first surgical implant implanted within a patient within an opening at a distal end of an elongate shaft such that a retention element disposed at least partially within the shaft directly contacts the first reduction tab;
manipulating the shaft to break the first reduction tab disposed within the opening; retaining the broken first reduction tab within the shaft;
disposing a second reduction tab of a U-shaped head of a second surgical implant implanted within the patient within the opening such that the retention element directly contacts the second reduction tab; manipulating the shaft to break the second reduction tab disposed within the opening; retaining the broken second reduction tab within the shaft; and
actuating a release mechanism that moves the retention element away from the opening to allow broken reduction tabs disposed within the chamber to be released from the shaft.

13. The method of claim 12, wherein at least a portion of the first reduction tab remains in direct contact with the retention element prior to the second reduction tab being disposed in the opening.

14. The method of claim 12, wherein the opening is configured to receive the second reduction tab therein without rotating the opening relative to the second surgical implant.

15. The method of claim 12, wherein the reduction tab disposed within the opening is broken by rotating the shaft about a longitudinal axis of the shaft.

16. The method of claim 15, wherein the shaft is angularly oriented relative to the first reduction tab and a torsional force is applied by the shaft to the first reduction tab to break the first reduction tab.

17. The method of claim 12, wherein the release mechanism is actuated by exerting a distal force on a proximal end of a movable end cap that is disposed on a proximal end of the shaft.

18. The method of claim 12, further comprising actuating a jam release bar that contacts a broken reduction tab disposed in the chamber and pushes the broken reduction tab out of the chamber when the release mechanism is actuated.

19. The method of claim 12, wherein actuating the release mechanism comprises rotating a cam to pivot the retention element away from the opening.

20. The method of claim 12, wherein actuating the release mechanism comprises sliding a bar distally along a surface of the retention element to pivot the retention element.

* * * * *